(12) United States Patent
Hedley et al.

(10) Patent No.: US 9,040,249 B2
(45) Date of Patent: May 26, 2015

(54) PAN-KINASE ACTIVATION AND EVALUATION OF SIGNALING PATHWAYS

(71) Applicants: Beckman Coulter, Inc., Brea, CA (US); University Health Network, Toronto (CA)

(72) Inventors: David Hedley, Toronto (CA); Sue Chow, Markham (CA); T. Vincent Shankey, Miami, FL (US)

(73) Assignees: Beckman Coulter, Inc., Brea, CA (US); University Health Network, Toronto (CA)

( * ) Notice: Subject to any disclaimer, the term of this patent is extended or adjusted under 35 U.S.C. 154(b) by 0 days.

(21) Appl. No.: 13/665,776

(22) Filed: Oct. 31, 2012

(65) Prior Publication Data

US 2013/0295582 A1 Nov. 7, 2013

Related U.S. Application Data

(63) Continuation of application No. 12/554,687, filed on Sep. 4, 2009, now abandoned.

(60) Provisional application No. 61/094,304, filed on Sep. 4, 2008.

(51) Int. Cl.
G01N 33/50 (2006.01)
G01N 33/573 (2006.01)
G01N 33/569 (2006.01)

(52) U.S. Cl.
CPC .......... *G01N 33/5008* (2013.01); *G01N 33/573* (2013.01); *G01N 33/5041* (2013.01); *G01N 33/5047* (2013.01); *G01N 33/56972* (2013.01)

(58) Field of Classification Search
None
See application file for complete search history.

(56) References Cited

U.S. PATENT DOCUMENTS

| | | | |
|---|---|---|---|
| 4,801,549 A | 1/1989 | Cremins et al. | |
| 5,496,734 A | 3/1996 | Sakata | |
| 5,597,688 A | 1/1997 | Connelly et al. | |
| 5,804,387 A | 9/1998 | Cormack et al. | |
| 5,968,738 A | 10/1999 | Anderson et al. | |
| 6,821,789 B2 | 11/2004 | Augello et al. | |
| 7,326,577 B2 | 2/2008 | Shults et al. | |
| 7,354,773 B2 | 4/2008 | Rubio et al. | |
| 7,381,535 B2 | 6/2008 | Perez et al. | |
| 7,521,297 B2 | 4/2009 | Lee et al. | |
| 7,563,584 B2 * | 7/2009 | Perez et al. | 435/7.2 |
| 7,695,924 B2 | 4/2010 | Perez et al. | |
| 7,695,926 B2 | 4/2010 | Perez et al. | |

(Continued)

OTHER PUBLICATIONS

Bland, J.M. et al., "Statistical Methods for Assessing Agreement Between Two Methods of Clinical Measurement." Lancet, 1:307-310, Elsevier, Holland (1986).

(Continued)

*Primary Examiner* — Gail R Gabel
(74) *Attorney, Agent, or Firm* — Merchant & Gould, P.C.

(57) ABSTRACT

Methods and reagents are provided for determining the activation state of a signal transduction pathway signaling protein. There exists a need in the art for methods that can monitor the efficacy of a signal transduction inhibitor in a patient. Other needs exist for detecting and monitoring certain disease or disorders that are associated with aberrant activation of a signal transduction pathway signaling protein. The present assay provides a highly sensitive assay that is also useful in patient populations in which obtaining a large cellular sample is difficult, for example, neonates.

24 Claims, 12 Drawing Sheets

(56) References Cited

U.S. PATENT DOCUMENTS

| | | | |
|---|---|---|---|
| 7,803,523 B2* | 9/2010 | Chow et al. | 435/2 |
| 8,148,054 B2 | 4/2012 | Kondoh | |
| 8,198,037 B2 | 6/2012 | Perez et al. | |
| 8,206,939 B2 | 6/2012 | Perez et al. | |
| 8,227,202 B2* | 7/2012 | Fantl et al. | 435/7.21 |
| 2005/0042688 A1 | 2/2005 | Hashemi | |
| 2006/0046272 A1 | 3/2006 | Chow et al. | |
| 2006/0073474 A1 | 4/2006 | Perez et al. | |
| 2006/0141549 A1 | 6/2006 | Mahajan et al. | |
| 2007/0004767 A1* | 1/2007 | Gutmann et al. | 514/291 |
| 2013/0034862 A1* | 2/2013 | Fantl et al. | 435/7.1 |

OTHER PUBLICATIONS

Bowers, R.K. et al., "A platelet biomarker for assessing phosphoinositide 3-kinase inhibition during cancer chemotherapy." Molecular Cancer Therapeutics, 6(9):2600-2607, Lilly Research Laboratories, United States (2007).

Chow, et al., "Toll-like Receptor-4 Mediates Lipopolysaccharide-induced Signal Transduction." The Journal of Biological Chemistry 274(16): 10689-10692 (Apr. 16, 1999).

Chow, S. et al., "Measurement of MAP Kinase Activation by Flow Cytometry Using Phospho-Specific Antibodies to MEK and ERK: Potential for Pharmacodynamic Monitoring of Signal Transduction Inhibitors." Cytometry, 46:72-78, Wiley-Lis, Inc., United States (2001).

Drevs, J. et al., "Receptor Tyrosine Kinases: The Main Targets for New Anticancer Therapy." Curr Drug Targets, 4:113-21, Tumor Biology Center, Germany (2003).

Fjallskog, M.H. et al., "Expression of Molecular Targets for Tyrosine Kinase Receptor Antagonists in Malignant Endocrine Pancreatic Tumors." Clin. Cancer Res., 9:1469-73, American Association for Cancer Research, United States (2003).

Francis, C. & M.C. Connelly, "Rapid Single-Step Method for Flow Cytometric Detection of Surface and Intracellular Antigens Using Whole Blood." Cytometry, 25:58-70, John Wiley & Sons, Inc., United States (1996).

Guha, M. & N. Mackman, "LPS induction of gene expression in human monocytes." Cellular Signaling, 13:85-94, Elsevier Science Inc., Holland (2001).

International Search Report for Application No. PCT/US2009/056088, European Patent Office, Netherlands, mailed on Sep. 4, 2009.

Kang, Y.J. et al., "Macrophage Deletion of p38 Partially Impairs Lipopolysaccharide-Induced Cellular Activation." The Journal of Immunology, 180:5075-5082, The American Association of Immunologists, United States (2008).

Kim et al., "Targeting the phosphatidylinositol-3 kinase/Akt pathway for the treatment of cancer." Curr. Opin. Investig. Drugs, 6(12): 1250-8, NCBI, United States (2005).

Kmet, L.M. et al., "A Review of p53 Expression and Mutation in Human Benign Low Malignant Potential, and Invasive Epithelial Ovarian Tumors." Cancer, 97:389-404, Department of Community Health Sciences, Canada (2003).

Krutzik et al., "Intracellular Phospho-protein Staining Techniques for Flow Cytometry: Monitoring Single Cell Signaling Events." Cytometry Part A 55A: 61-70 (2003).

Lang, C.H. et al., "Regulation of muscle protein synthesis during sepsis and inflammation." Am. J. Physio. Endocrinol. Metab., 293:453-459, The American Physiological Society, United States (2007).

Loken, M.R. et al., "Establishing Optimal Lymphocyte Gates for Immunophenotyping by Flow Cytometry." Cytometry, 11:453-459, Wiley-Liss, Inc., United States (1990).

Mullins, J. Michael, "Overview of Flurophores." Methods Mol Biol, 34:107-16, Humana Press, United States (1994).

Petit, J.M. et al., "Assessment of flurochromes for celluar structure and function studies by flow cytometry." Biol. Cell, 78:1-13, Institut de Biotechnologie, France (1993).

Riley, J., "Fisher Distances and Applications to Measures of Similarity" in Statistical Analysis and Optimal Classification of Blood Cell Population Using Gaussian Distributions, Ph.D. dissertation, Chp. 5, pp. 43-56 Florida International University, United States (2003).

Shapiro, Howard M., "Optical Measurements in Cytometry" Light Scattering Extinction, Absorption, and Fluorescence. Methods Cell Biol, 63:107-129, Elsevier, Holland (2001).

Tashiro et al., "Overexpression of Cyclin D1 Contributes to Malignancy by Up-Regulation of Fibroblast Growth Factor Receptor 1 via the pRB-E2F Pathway." Cancer Res, 63:424-431, Department of Biosciences and Informatics, Japan (2003).

West, M.A. et al., "Whole Blood Leukocyte Mitogen Activated Protein Kinases Activation Differentiates Intensive Care Unit Patients with Systemic Inflammatory Response Syndrome and Sepsis." The Journal of Trauma Injury, Infection, and Critical Care, 62:805-811, Lippincott Williams & Wilkins, United States (2007).

Wiese, A. et al., "The dual role of lipopolysaccharide as effector and target molecule." Biol. Chem., 380:767-84, NCBI, United States (1999).

Zhao, J. et al., "Rapid and quantitative detection of p38 kinase pathway in mouse blood monocyte." InVitro Cell. Dev. Biol., 44:145-153, The Society for in Vitro Biology, United Sates (2008).

Chinese Decision of Rejection mailed Oct. 22, 2014, for corresponding Chinese Patent Application 200980135080.9, English translation.

Chinese Decision of Rejection (English translation) mailed Oct. 22, 2014, for corresponding Chinese Patent Application 200980135080.9.

Chow et al., "Constitutive phosphorylation of the S6 ribosomal protein via mTOR and ERK signaling in the peripheral blasts of acute leukemia patients"; Experimental Hemotology, 34(9):1182-1190 (Sep. 1, 2006).

Chow et al., "Whole Blood Processing for Measurement of Signaling Proteins by Flow Cytometry", Curr Protoc Cytom, 9(9.27) (Oct. 1, 2008).

Extended European Search Report mailed Jan. 18, 2012, for corresponding European Patent Application 09812308.6. (Now Granted as Patent No. 2318836).

Gavasso et al., "Multiplexed phosphoprotein analysis in immune cells", Acta Neurologica, 113(s183):58-60 (May 1, 2006).

Hedley et al., "Pharmacodynamic Monitoring of Molecular-Targeted Agents in the Peripheral Blood of Leukemia Patients Using Flow Cytometry"; Toxicologic Pathology, 36(1):133-139 (Jan. 1, 2008).

Perez et al., "Simultaneous measurement of multiple active kinase states using polychromatic flow cytometry", Nature BioTechnology, 20:155-162 (Feb. 1, 2002).

* cited by examiner

Figure 1 - LPS Stimulation of MAPK and NF-κB

Figure 5 – Kinetics of LPS response at 6 minutes

Figure 6 – Kinetics of LPS response at 60 minutes

PAN-KINASE ACTIVATION AND EVALUATION OF SIGNALING PATHWAYS

CROSS-REFERENCE TO RELATED APPLICATIONS

This patent application is a continuation and claims the benefit of priority pursuant to 35 U.S.C. §120 to U.S. patent application Ser. No. 12/554,687, filed Sep. 4, 2009, a U.S. Non-Provisional Patent Application that claims priority to U.S. Provisional Application 61/094,304, filed Sep. 4, 2008, each of which is hereby incorporated by reference in its entirety.

BACKGROUND OF THE INVENTION

1. Field of the Invention

Certain embodiments of the invention relate to methods for determining the activation state of a signal transduction pathway signaling protein. In at least some embodiments, methods are provided for monitoring the efficacy of a signal transduction inhibitor in a patient. The present invention further provides highly sensitive assays useful in patient populations in which obtaining a large cellular sample is difficult, for example, neonates. Certain embodiments of the invention relate to methods of identifying novel signal transduction pathway protein inhibitors. Certain embodiments of the invention relate to methods for detecting sepsis in a patient sample. Kits for practicing the methods of the invention are also provided.

2. Background

Many diseases are characterized by disruptions in cellular signaling pathways that lead to pathologies including uncontrolled growth and proliferation of cancerous cells, as well as aberrant inflammation processes. Such defects can include changes in the activity of lipid kinases, a class of enzymes that catalyze the transfer of phosphate groups to lipids. These phosphorylated lipids, in turn, recruit downstream proteins that propagate the signals originating from upstream signaling mediators, such as receptor tyrosine kinases and antigen receptors. For example, the protein kinase Akt is recruited by phospholipids to the plasma membrane where it is activated. Once activated, Akt plays a pivotal role in survival both of normal and cancerous tissues.

Phosphoinositide 3-kinases (PI3Ks) are a family of lipid kinases that play pivotal roles in signaling pathways downstream from multiple cell surface receptors, controlling growth, proliferation, and cell survival. Active PI3Ks consist of two subunits: a regulatory subunit with a molecular weight of either 85 or 55 kD (p85 or p55), and a catalytic subunit of molecular weight 110 kD (p110). While the regulatory subunits are critical to the function of PI3K, these regulatory subunits also transmit signals independently of PI3-kinase (Ueki et al., J. Biol. Chem. November 28; 278(48): 48453-66 (2003)). It has recently been demonstrated that p85-alpha can induce apoptosis via the inducible transcription factor NFAT3 independent of the PI3K signaling pathway (Song et al., Mol. Cell. Biol. 27: 2713-2731 (2007)).

The PI3K pathway is implicated in various human diseases including diabetes, heart failure, and many cancers (see e.g., Kim et al., Curr. Opin. Investig. Drugs. December; 6(12): 1250-8 (2005)) including colorectal cancer, acute myeloid leukemia, breast cancer, gliomas, and ovarian cancer. Inhibitors of PI3K are being studied as potential therapeutics in a variety of diseases including cancer, heart failure and autoimmune/inflammatory disorders.

The mitogen activated protein kinase (MAPK) signal transduction pathway is also involved in cell proliferation and differentiation. This pathway plays a role in regulating oocyte meiotic maturation (Moriguchi et al., Adv. Pharmacol. 36:121-137 (1996); Murakami et al., Methods in Enzymology 283:584-600 (Dunphy, ed., 1997); Matten et al., Seminars in Dev. Biol. 5:173-181 (1994)).

The MAPK pathway is also involved in the regulation of cell growth, survival, and differentiation (Lewis et al., supra). Furthermore, activated MAPK and/or elevated level of MAPK expression have been detected in a variety of human tumors (Hoshino, R. et al., Oncogene 18:813-822 (1999); Salh, B. et al., Anticancer Res. 19:741-48 (1999); Sivaraman, V. S. et al., J. Clin. Invest. 99:1478-483 (1997); Mandell, J. W et al., Am. J. Pathol. 153:1411-23 (1998); Licato, L. L. et al. Digestive Diseases and Sciences 43, 1454-1464 (1998)) and may be associated with invasive, metastatic and angiogenic activities of tumor cells. Thus, inappropriate activation of the MAPK pathway is an essential feature common to many types of tumors. For this reason, participants in this signaling pathway, such as MEK, are potential targets for cancer therapy.

Several groups have developed assays to monitor inhibitors of various signal transduction pathways. One assay, which detects the activity of inhibitors of the PI3K>Akt pathway, uses peripheral blood platelets (Bowers et al., Mol. Cancer Ther. 6:2600-2607 (2007)). However, this assay only measures the impact of inhibition of this pathway (inhibition of platelet activation), and does not directly monitor phosphorylation (activation) of the target signaling proteins. In addition, technical difficulties make measurement of this pathway using peripheral blood platelets challenging.

Similarly, West et al. (J. Trauma Injury, Inf. and Crit Care 62:805-811 (2008)) reported a flow cytometry based assay to detect sepsis, using the lack of peripheral blood monocyte activation (measured by phosphorylation of p38 and ERK) following in vitro exposure to lipopolysacharide (LPS). However, this assay did not confirm specificity, and did not note the early ERK activation or the secondary activation of all three MAPK pathways. This assay was also susceptible to unacceptably high background levels for a clinically-relevant assay. For example, from their results, the authors conclude that in normal controls, the percent of monocytes expressing phospho-ERK increases from 35% without LPS stimulation, to 58% positive after LPS treatment in vitro (measured at one 15 min time point after LPS addition). In contrast, presumably septic patients showed 25% P-ERK monocytes before LPS addition, which increased less than 10% following LPS addition in vitro.

BRIEF SUMMARY OF THE INVENTION

A need in the art exists for an assay that can accurately monitor the efficacy of a signal transduction inhibitor in a patient. Other needs exist for detecting and monitoring certain disease or disorders that are associated with aberrant activation of a signal transduction pathway signaling protein. Current assays rely on immunoblotting techniques that cannot identify the actual cell-type generating the response in a mixed cell population. Also, by having to remove the drug from the samples, these assays are cumbersome and are subject to a lack of sensitivity. Sensitive assays are especially needed in patients in which obtaining a large sample is difficult, for example, in neonates.

In one embodiment, the present invention provides a method for determining the activation state of a signal transduction pathway signaling protein in a leukocyte-containing sample (i.e., a blood sample) comprising: a) activating the activatable proteins of at least one signal transduction pathway in the leukocytes of the sample by exposing the sample to a pan-kinase activator; b) preserving the sample with a preservative; c) unmasking intracellular epitopes of the preserved leukocytes in the sample; d) contacting the unmasked intracellular epitopes of the preserved leukocytes with a plurality of fluorescently labeled capture molecules, said plurality of capture molecules comprising at least two different capture molecules capable of binding to the activated state of at least two different unmasked intracellular epitopes of preserved, activated leukocytes in the sample and at least one control capture molecule, wherein the control capture molecule binds to an epitope on the preserved leukocytes that is unactivated (i.e., non-activated) by the pan-kinase activator; e) detecting fluorescence of the preserved, activated leukocytes captured by the binding of the capture molecules to the activated state of the unmasked intracellular epitopes; f) detecting fluorescence of the preserved leukocytes captured by the binding of the control capture molecule; and g) comparing the fluorescence of the detected preserved, activated leukocytes captured by the capture molecules to the fluorescence of the detected preserved leukocytes captured by the capture molecules.

In certain embodiments, the method further comprises evaluating the compared fluorescence measured in step g) to compared fluorescence measured in an unactivated reference sample.

In other embodiments, the method is such that wherein the sample is from a patient and the evaluation of the fluorescence indicates that the patient has a signal transduction associated disease or condition when the fluorescence of the activated and unactivated samples are approximately comparable.

In at least some embodiments, the method comprises repeating steps a) to g) with a sample from the patient after the patient has received a therapeutic agent to treat inflammation, fever, sepsis, cancer, diabetes, or heart failure and monitoring the effectiveness of that therapeutic agent by monitoring for a change in the detected fluorescence between the activated and unactivated samples.

The present invention further provides methods wherein the evaluating of the detected fluorescence indicates that the kinase inhibitor is effective in treating the signal transduction associated disease or condition patient when a change is determined in the detected fluorescence between the activated and unactivated samples.

The present invention provides methods wherein the sample has been exposed to a putative kinase inhibitor and the method further comprises ascertaining the effectiveness of the kinase inhibitor when the activated sample does not demonstrate a change in fluorescence of the activatable proteins of the at least one signal transduction pathway.

Also provided by the present invention are kits for monitoring signal transduction inhibition comprising: a pan kinase activator; and at least two capture molecules that bind at least one signal transduction pathway proteins selected from the group consisting of P38, ERK, PI3K, and ribosomal S6.

Further embodiments, features, and advantages of the invention, as well as the structure and operation of the various embodiments, are described in detail below with reference to the accompanying figures.

BRIEF DESCRIPTION OF THE FIGURES

The accompanying figures, which are incorporated herein and form a part of the specification, illustrate one or more embodiments of the invention and, together with the description, further serve to explain the principles of the invention.

DETAILED DESCRIPTION OF THE INVENTION

Overview

Figure 1:
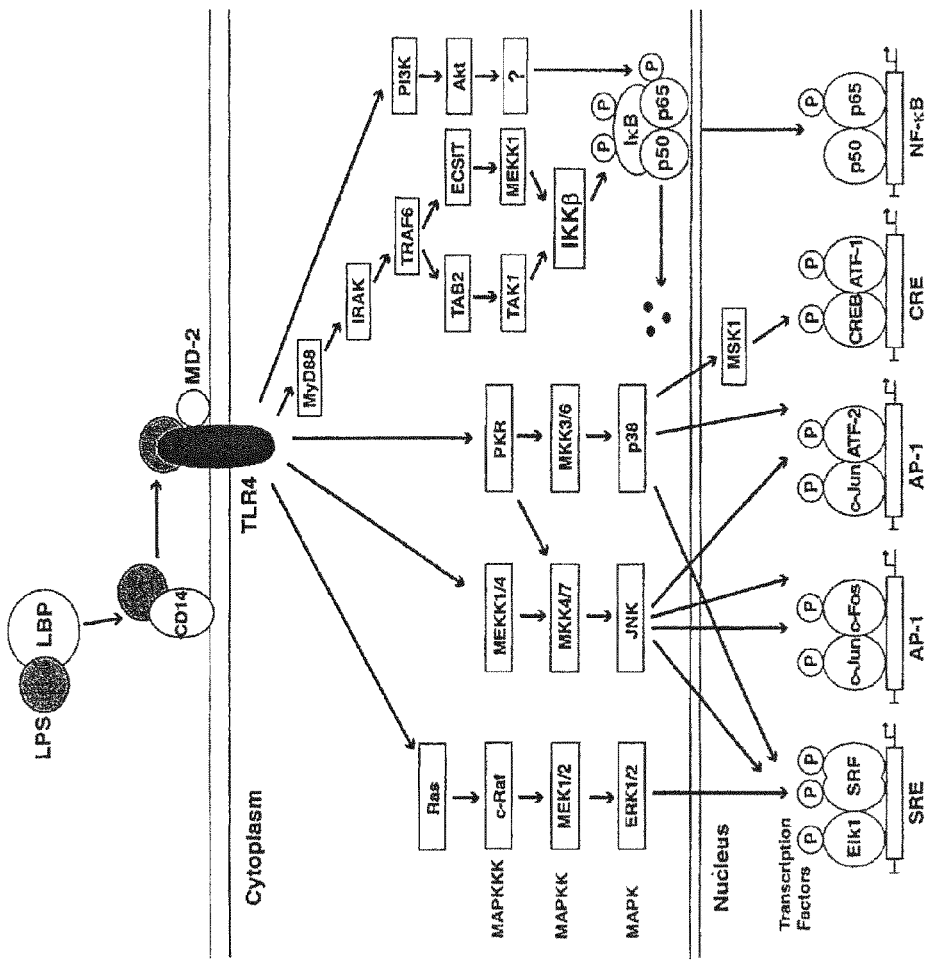
FIG. 1 shows a general schematic of intracellular activation by lipopolysaccharide (LPS) in monocytes.

In one embodiment, the invention relates to methods for determining the activation state of a signal transduction pathway signaling protein in a leukocyte-containing sample. Other embodiments provide methods of monitoring the efficacy of a signal transduction inhibitor in a patient or test sample. In certain embodiments, the methods provide a highly sensitive assay that is also useful in patient populations in which obtaining a large cellular sample is difficult, for example, neonates. In another embodiment, the invention relates to methods of identifying novel signal transduction pathway protein inhibitors. In a further embodiment, the invention relates to methods for detecting sepsis in a patient sample. Kits for practicing the methods of the invention are also provided.

A significant advantage of the present invention is that the increased specificity and sensitivity allows for use of the methods with very small sample sizes. This is important where only a small patient sample is obtainable, for example, with neonates.

It should be noted that as used herein and in the appended claims, the singular forms "a," "and," and "the" include plural references unless the context clearly dictates otherwise.

Although any methods, devices, and materials similar or equivalent to those described herein can be used in the practice of the invention, the particular methods, devices, and materials are now described.

Preparation of the Test Sample

The terms test sample and sample are used interchangeably herein. The test sample in the methods of the present invention can include any leukocyte-containing sample, for example, whole blood, blood plasma, bone marrow aspirates (or any cells obtained from bone marrow), urine, serum, saliva, cerebral spinal fluid, urine, amniotic fluid, interstitial fluid, feces, mucus, body tissue extracts or cellular extracts. In certain embodiments, the sample is a blood sample. In a preferred embodiment, the blood sample is whole blood. The whole blood can be obtained from the individual or test subject using standard clinical procedures.

Obtaining a blood sample encompasses obtaining the blood sample directly from the patient, for example by a phlebotomist. Obtaining a blood sample also encompasses obtaining a blood sample that was previously obtained from a patient, for example a laboratory technician obtaining a patient's blood sample for analysis using the methods of the present invention. Plasma can be obtained from whole blood samples by centrifugation of anti-coagulated blood. Such a process provides a bottom layer of packed red blood cells, an intermediate buffy coat layer and a supernatant plasma layer.

Leukocytes can be isolated from whole blood samples by any of various techniques including buoyant density centrifugation and others known in the art. The leukocytes, i.e., white blood cells, comprise monocytes, lymphocytes, neutrophils, basophils, and eosinophils. Monocytes are especially preferred for use in the methods of the present invention.

Samples can be obtained from a human person or a commercially significant mammal, including but not limited to a monkey, cow, or horse. Samples can also be obtained from household pets, including but not limited to a dog or cat.

In some embodiments, the sample is obtained from a "naive patient." By "naive patient" is meant one who has not undergone treatment with a signal transduction pathway protein inhibitor. In certain embodiments, the sample is obtained from a "naive patient" that is an age-matched control. By "age-matched" is meant a sample from a naive patient of similar age. In certain embodiments, the "age-matched" samples are obtained from an individual of similar age, sex, and race. In some embodiments, age-matched leukocytes from normal individuals are used as negative controls to correlate signal transduction pathway protein activity.

In some embodiments, the sample is treated with an anticoagulant. Examples of anticoagulants include, but are not limited to, vitamin K inhibitors such as warfarin, EDTA (ethylenediaminetetraacetic acid), ACD (acid-citrate-dextrose), heparin, and 1,3-indanediones.

Signal Transduction Pathway Activation

As used herein, an "activatable signal transduction pathway protein," or its grammatical equivalent, refers to a protein that has at least one isoform (and in some cases two or more isoforms) that corresponds to a specific form of the protein having a particular biological, biochemical, or physical property, e.g., an enzymatic activity, a modification (e.g., post-translational modification), or a conformation. The activatable protein can be activated or unactivated (i.e., non activated) with respect to a particular biological activity, modification, or conformation. Specifically, the activated or active form of the activatable signal transduction pathway protein has the particular biological activity, modification, or conformation, whereas the unactivated or unactive (non-active) form of the activatable signal transduction pathway protein does not have (or has a lesser or diminished level of) the particular biological activity, modification, or conformation, respectively. In some embodiments, there can be more than one isoform associated with an activity or activation state; for example, there can be an isoform associated with an "open" conformation available for substrate binding, a second transition state isoform, and an isoform devoid of activity (e.g., where the activity is inhibited).

In a certain embodiment, the biological, biochemical, or physical property (e.g. enzymatic activity, modification, or conformation) of the activatable signal transduction pathway protein is inducible or activatable by an activating agent or by cell signaling events. Examples of activating agents include, but are not limited to, kinases, phosphatases, proteases (e.g., caspases), and hormones. Examples of cell signaling events include, but are not limited to, receptor clustering or binding of a cognate molecule or ligand.

As used herein, an isoform refers to a form of an activatable protein having a specific, and preferably detectable, biological activity, modification, or conformation. The isoform can be an activated (or active) form, or unactivated (or not active) form of an activatable receptor. As mentioned, in certain embodiments, the binding of an activation state-specific capture molecule (such as an antibody) to a corresponding isoform of an activatable receptor element is indicative of the identity of the activatable receptor element and of the activation state of the activatable receptor element. In a certain embodiment, the invention provides methods for determining a receptor element isoform profile which comprise determining the presence of an isoform of an activatable receptor element that is activated (or activated isoform).

In a certain embodiment, the activated isoform or activated state of an activatable receptor element is a form of the activatable receptor having a particular or specific biological, biochemical, or physical property that is not possessed by at least one other isoform of activatable receptor element.

Examples of such properties include, but are not limited to, enzymatic activity (e.g., kinase activity and protease activity), and receptor element binding activity. Thus, such particular or specific properties or activities are associated with an activated isoform of an activatable receptor element. Such properties or activities are sometimes referred to herein as activation state activities.

An example of activation state activity is kinase activity for an activated receptor element. As used herein, a signal transduction pathway protein with protein kinase activity refers to signal transduction pathway protein that when activated is capable of catalyzing the phosphorylation of amino acids, or derivatives thereof, which possess an hydroxyl group. Preferred kinases are those that are capable of catalyzing the phosphorylation of serine, threonine, and tyrosine residues. Kinase activity can be determined by supplying a substrate for phosphorylation by kinase, a source of phosphate usable by kinase, and determining the phosphorylation of substrate in the presence of kinase.

The antigenicity of an activated isoform of an activatable receptor element is distinguishable from the antigenicity of non-activated isoform of an activatable receptor element or from the antigenicity of an isoform of a different activation state. In a certain embodiment, an activated isoform of a receptor element possesses an epitope that is absent in a non-activated isoform of a receptor element, or vice versa. In another embodiment, this difference is due to covalent addition of moieties to a receptor element, such as phosphate moieties, or due to a structural change in a receptor element, as through protein cleavage, or due to an otherwise induced conformational change in a receptor element which causes the element to present the same sequence in an antigenically distinguishable way. In another embodiment, such a conformational change causes an activated isoform of a receptor element to present at least one epitope that is not present in a non-activated isoform, or to not present at least one epitope that is presented by an unactivated (i.e., non-activated) isoform of the element. In some embodiments, the epitopes for the distinguishing capture molecules are centered around the active site of the receptor element, although as is known in the art, conformational changes in one area of a receptor element can cause alterations in different areas of the element as well.

In certain embodiments, the signal transduction pathway is the mitogen activated protein kinase (MAPK) pathway, which is a signal transduction pathway that effects gene regulation, and which controls cell proliferation and differentiation in response to extracellular signals. This pathway is also involved in oocyte meiotic maturation. The MAPK pathway is found, e.g., in frogs, and in mammals, e.g., mice, rats, and humans. This pathway can be activated by cytokines such as IL-1 and TNF, and constitutively activated by proteins such as Mos, Raf, Ras, and V12HaRas.

In other embodiments, the signal transduction pathway is the PI3K pathway. The PI3K pathway is a phosphatidylinositol 3-kinase pathway which mediates and regulates cellular apoptosis. The PI3K pathway also mediates cellular processes, including proliferation, growth, differentiation, motility, neovascularization, mitogenesis, transformation, viability, and senescence. The cellular factors that mediate the PI3K pathway include PI3K, Akt, and BAD. These factors mediate and regulate cellular apoptosis. The PI3K factors include class I PI3K, a cystolic enzyme complex which includes p85 and p110. BAD has been identified as a pro-apoptotic member of the bcl-2 family.

Ribosomal protein S6 (RPS6) belongs to S6E family of ribosomal proteins and it is involved in the control of cell growth and proliferation via selective translation (Molina H. et al.; Proc. Natl. Acad. Sci. USA 104:2199-2204, (2007)). It is a major substrate of Ribosomal Protein S6 Kinase (RSK) in eukaryote ribosomes. During translation, it regulates the translation of any RNA which contains 5' terminal oligopyrimidine sequence (5'TOP). 5'TOP encodes proteins for cell cycle progression, ribosomal proteins, and elongation factors. The phospholyation of RPS6 has been linked to increase in selective 5'TOP translation. The major phospholyation sites in RPS6 includes Ser235, 236, 240, and 244 (Peterson, R. T. and Schreiber, S. L., 1998). The phospholyation of RPS6 is stimulated by growth factors, tumor promoting agents, and mitogens. During growth arrest, RPS6 is dephoshorylated.

In certain embodiments, the Signal Transduction Pathway Protein is PI3K ribosomal S6 protein, p44/42 MAP kinase, TYK2, p38 MAP kinase, PKC, PKA, SAPK, ELK, JNK, cJun, RAS, Raf, MEK 1/2, MEK 3/6, MEK 4/7, ZAP-70, LAT, SRC, LCK, ERK 1/2, Rsk 1, PYK2, SYK, PDK1, GSK3, FKHR, AFX, PLCg, PLCy, FAK, CREB, $\alpha$III$\beta$3, Fc$\epsilon$RI, BAD, p70S6K, STAT1, STAT2, STAT3, STAT5, STAT6, or combination of these proteins. In particular embodiments, signal transduction pathway proteins are P38 and ERK and PI3K or ribosomal S6. Other embodiments are where the signal transduction pathway proteins are P38, ERK, and ribosomal S6. JNK and ribosomal S6 provide other signal transduction pathway proteins suitable for use in the methods of the present invention.

In certain embodiments, the sample is incubated with a pan-kinase activator. In certain embodiments, the pan-kinase activator is lipopolysaccharide (LPS). The term "LPS" will be understood to encompass naturally occurring and synthetically or semi-synthetically prepared variants.

LPS consists of a lipid component, lipid A, and a polysaccharide unit covalently linked in the membrane domain. The polysaccharide region consists of the terminal O-specific chain, a substructure that comprises up to 50 repeating oligosaccharide units of usually two to eight monomers, and the core region, which is linked to the lipid A.

The O-specific chain is characterized by extreme structural variability in different species. The lipid A component is responsible for the biological activity described below. The biological activity is modulated by variation of the acylation pattern of the lipid A. This activity ranges from an agonistic effect, such as occurs with most naturally occurring LPS variants (e.g., Salmonella friedenau or Salmonella abortus equi), to the antagonistic effect of the LPS variants of plant-symbiotic microorganisms or synthetic derivatives (C. Alexander and E. T. Rietschel, Biospektrum, Vol. 4, No. 5, pp. 275-281, 1999). A comprehensive description of LPS may also be found in A. Wiese, K. Brandenburg, U. Seydel, and S. Muller-Leoennies: The Dual Role of Lipopolysaccharide as Effector and Target Molecule. Biol. Chem., 380, pp. 767-784.

Lipopolysaccharides are formed by gram-negative bacteria and are highly potent stimulators of innate immunity. They bind to toll-like receptor 4 (TLR4)/CD14 receptors on human mononuclear cells (see FIG. 1) and induce the formation and secretion of pro-inflammatory cytokines, such as TNF$\alpha$, MIF, IL-1$\beta$, IL-6, IL-8, IL-12, IL-15 and IL-18, various colony-stimulating factors, various lipid mediators, and reduced oxygen species.

Lipopolysaccharides also activate the nonspecific immune response by these mechanisms, and microorganisms, viruses, and tumor cells can be better eliminated as a result of this response. Phenomena such as inflammation, fever and sepsis are induced by the LPS-induced production of cytokines and lipid mediators. Due to the toxic effect of LPS in sepsis, agonistic LPS are also called endotoxins.

In other embodiments, the pan-kinase activator is a TLR4 activator. Other surface tyrosine kinase receptor activators can be used in the invention to stimulate other pathways in monocytes, e.g. GM-CSF to activate the JAK/STAT pathway in peripheral blood monocytes, or agonists such as IL-4 to activate JAK/STAT pathway in peripheral blood lymphocytes.

Optimal incubation times and temperatures for each sample preparation step can be readily determined using routine experimentation. In at least one embodiment, activation by the pan-kinase activator is performed for about 1 to 10 minutes. During this period, early activating signal transduction pathway signaling proteins can be monitored. For example, as demonstrated in the following examples, activation of ERK is measurable within 2 minutes of exposure to the pan-kinase activator. Other activating signal transduction pathway signaling proteins reach saturation within about 15 minutes from exposure to the pan-kinase activator.

In other embodiments, activation by the pan-kinase activator is performed for greater than about 30 minutes. During this period, late activating signal transduction pathway signaling proteins can be monitored. For example, as demonstrated in the following examples, ribosomal S6 signaling begins to peak sometime after 30 minutes of exposure to the pan-kinase activator.

Preservation and Unmasking Methods

In one embodiment, the invention provides a method for preparing a biological sample for measurement of protein epitopes that preserves intracellular protein epitopes for subsequent detection. The method encompasses a preservation (fixation) step that includes contacting said sample with a preservative (fixative) in an amount to achieve a final concentration sufficient to crosslink proteins, lipids, and nucleic acid molecules; a detergent step that encompasses addition of a detergent to the biological sample in an amount to achieve a final concentration sufficient to lyse any red blood cells present in the sample and permeabilize the white blood cells; and a labeling step, wherein the sample is contacted with a detectable binding agent specific for a one or more epitopes. Specific methods are described in co-pending U.S. application Ser. No. 10/928,570, which is herein incorporated by reference.

To the extent that the sample does not contain red blood cells, i.e., the sample has been previously fractionated, it is understood that the lysis step is unnecessary.

In one embodiment, the invention provides a method for preparing a biological sample for measurement of protein epitopes that preserves signal pathway protein epitopes for subsequent detection. The method encompasses a preservation (fixation) step that includes contacting the sample with a preservative (fixative) in an amount to achieve a final concentration sufficient to crosslink proteins, lipids and nucleic acid molecules. The preservative (fixative) concentration can be between approximately 0.1 percent and approximately twenty percent, between approximately 0.5 percent and approximately 15 percent; between approximately 1 percent and approximately 10 percent, between approximately 1 percent and approximately 8 percent, between approximately 1 percent and approximately 4 percent, between approximately 1 percent and approximately 2 percent. The preservative (fixative) can be added either in concentrated solution or in diluted form to achieve the desired concentration. The preservative (fixative) can be any appropriate agent desired by the user, for example, aldehyde, formaldehyde, or paraformaldehyde, or formalin.

The method of the invention for preparing a biological sample for measurement of protein epitopes that preserves intracellular protein epitopes for subsequent detection further encompasses a detergent step, wherein detergent is added in an amount to achieve a final concentration sufficient to lyse any present red blood cells and permeabilize white blood cells. The detergent concentration can be selected by the user based on a variety of conditions and can be in a range of between approximately 0.1 percent and approximately 10 percent; between approximately 0.1 percent and approximately 8 percent; between approximately 0.1 percent and approximately 7 percent; between approximately 0.1 percent and approximately 6 percent; between approximately 0.1 percent and approximately 5 percent; between approximately 0.1 percent and approximately 4 percent; between approximately 0.1 percent and approximately 3 percent; between approximately 0.1 percent and approximately 2 percent; between approximately 0.1 percent and approximately 1 percent.

The detergent can be selected based on a variety of factors and can be an ionic or a non-ionic detergent. Detergents are preferably selected from among non-ionic detergents. One currently preferred detergent is ethyoxylated octylphenol, which is referred to by the commercial name of TRITON X-100 (Sigma T9284). In preferred embodiments, the methods are practiced with TRITON X-100. Suitable detergents for the invention methods can permeabilize cells and retain surface epitope integrity. Ionic detergent useful in the invention further include octylphenoxypoly(ethyleneoxy)ethanol, commercially available as IGEPAL® CA-630 (Sigma N-6507) or Nonidet P-40 (NP-40) (Sigma), Brij-58, and linear alcohol alkoxylates, commercially available as PLURAFAC® A-38 (BASF Corp) or PLURAFAC® A-39 (BASF Corp).

In complex cell populations such as, for example, undiluted peripheral blood, bone marrow aspirate, and peritoneal fluid, it can be useful to distinguish cell subsets by surface markers and detect intracellular phospho-epitope staining in one procedure. The methods provided by the present invention for preparing a red blood cell containing biological sample for measurement of protein epitopes that preserves intracellular protein epitopes for subsequent detection are amenable to be used for combining intracellular epitope detection with detection of cell surface epitopes. In the method provided by the invention, both intracellular and extracellular epitopes can remain intact so as to allow subsequent measurement by cytometric analysis. For example, the surface detection of typical monocyte markers including, for example, CD14 can be combined with intracellular epitope detection.

In a further embodiment, the method encompasses a further alcohol step that encompasses contacting the biological sample with alcohol in an amount to achieve a final concentration sufficient to unmask cellular epitopes that are lost due to cross-linking during the fixation step. As described herein, the alcohol step can preserve the majority of extracellular epitopes and can be adjusted by the user in length of incubation, temperature and concentration depending on the epitopes to be preserved.

A final alcohol concentration based on other variables including, for example, incubation time, temperature and particular epitopes targeted for unmasking and measurement can be readily selected. The final alcohol concentration can be between approximately 25 percent and approximately 75 percent, between approximately 30 percent and approximately 70 percent, between approximately 35 percent and approximately 65 percent, between approximately 40 percent and approximately 60 percent, between approximately 45 percent and approximately 55 percent. The alcohol can further be selected from the group consisting of ethanol and methanol. If desired, acetone can be substituted for alcohol in the alcohol step. The sample can be contacted with alcohol or acetone at a temperature, for example, approximately −30 degrees Celsius, approximately −20 degrees Celsius, approximately −10 degrees Celsius, approximately −5 degrees Celsius, approximately 0 degrees Celsius, approximately 4 degrees Celsius, approximately 6 degrees Celsius, approximately 8 degrees Celsius, or any other temperature that facilitates the unmasking of intracellular epitopes without reducing the reactivity of cell surface epitopes.

Capture Molecules and Other Agents of the Invention

In one embodiment of the invention, the signal transduction pathway protein is activated to propagate a signal. The levels of signal transduction pathway proteins are generally determined using capture molecules. As used herein, the term "capture molecule" refers to any molecule or complex of molecules capable of binding to a signal transduction pathway protein of the invention under suitable conditions. Thus, a capture molecule, includes any molecule, e.g., protein, small organic molecule, carbohydrates (including polysaccharides), polynucleotide, lipids, etc. The selection of those conditions is well known, as well as techniques to vary or modify the binding conditions. For example, it is well known that temperature, pH and time of incubation all play a role in binding. Generally, the binding occurs with sufficient specificity to exclude significant binding to more than one ligand. In some embodiments of the invention, the capture molecule is an antibody or ligand binding fragment or analog thereof. The capture molecule can also be other proteins or nucleic acids, or portions or analogs thereof, that bind signal transduction pathway protein in the practice of certain embodiments of the invention.

In preferred embodiments, the capture molecules are antibodies, especially monoclonal antibodies. The term antibody as used herein refers to immunoglobulin molecules and immunologically active portions of immunoglobulin (Ig) molecules. Such antibodies include, but are not limited to, polyclonal, monoclonal, mono-specific polyclonal antibodies, antibody mimics, chimeric, single chain, Fab, Fab' and F(ab')$_2$ fragments, Fv, and an Fab expression library. In general, an antibody molecule obtained from humans relates to any of the classes IgG, IgM, IgA, IgE and IgD, which differ from one another by the nature of the heavy chain present in the molecule. Certain classes have subclasses as well, such as IgG1, IgG2, and others. Furthermore, in humans, the light chain can be a kappa chain or a lambda chain. Reference herein to antibodies includes a reference to all such classes, subclasses and types of antibody species.

It has been shown that fragments of an antibody can perform the function of binding antigens. As used herein "antigen binding fragments" includes, but is not limited to: (i) the Fab fragment consisting of $V_L$, $V_H$, $C_L$ and $C_{H1}$ domains; (ii) the Fd fragment consisting of the $V_H$ and $C_{H1}$ domains; (iii) the Fv fragment consisting of the $V_L$ and $V_H$ domains of a single antibody; (iv) the dAb fragment which consists of a $V_H$ domain; (v) isolated CDR regions; (vi) F(ab')$_2$ fragments (vii) single chain Fv molecules (scFv), wherein a $V_H$ domain and a $V_L$ domain are linked by a peptide linker which allows the two domains to associate to form an antigen binding site (Bird et al., Science 242:423-426 (1988); Huston et al., Proc. Natl. Acad. Sci. USA 85:5879-5883 (1988)); (viii) bispecific single chain Fv dimers (PCT/US92/09965) and (ix) diabodies, multivalent or multispecific fragments constructed by gene fusion (WO94/13804; P. Holliger et al., Proc. Natl. Acad. Sci. USA 90:6444-6448 (1993)).

The capture molecules of the invention can comprise a fluorescent label. By fluorescent label is meant a molecule that can be directly (i.e., a primary label) or indirectly (i.e., a secondary label) detected; for example a label can be visualized and/or measured or otherwise identified so that its presence or absence can be known. A compound can be directly or indirectly conjugated to a label which provides a detectable signal, e.g. fluorescers, enzyme, antibodies, particles such as magnetic particles, chemiluminescers, or specific binding molecules, etc. Specific binding molecules include pairs, such as biotin and streptavidin, digoxin and antidigoxin, etc. Labels include, but are not limited to, fluorescent labels and enzymes.

In general, labels can be colored or luminescent dyes or moieties; and binding partners. Labels can also include enzymes (horseradish peroxidase, etc.) and magnetic particles. In a certain embodiment, the detection label is a primary label. A primary label is one that can be directly detected, such as a fluorophore.

In certain embodiments, the labels include chromophores or phosphors but are preferably fluorescent dyes or moieties. Fluorophores can be either "small molecule" fluores, or proteinaceous fluores.

By fluorescent label is meant any molecule that can be detected via its inherent fluorescent properties. Suitable fluorescent labels include, but are not limited to, fluorescein, rhodamine, tetramethylrhodamine, eosin, erythrosin, coumarin, methyl-coumarins, pyrene, Malacite green, stilbene, Lucifer Yellow, Cascade Blue™, Texas Red, IAEDANS, EDANS, BODIPY FL, LC Red 640, Cy 5, Cy 5.5, LC Red 705 and Oregon green. Suitable optical dyes are described in the 1996 Molecular Probes Handbook by Richard P. Haugland, herein incorporated by reference. Suitable fluorescent labels also include, but are not limited to, green fluorescent protein (GFP; Chalfie et al., Science 263(5148):802-805 (1994); and EGFP; Clontech—Genbank Accession Number U55762), blue fluorescent protein (BFP; 1. Quantum Biotechnologies, Inc., 1801 de Maisonneuve Blvd. West, 8$^{th}$ Floor, Montreal (Quebec) Canada H3H 1J9; 2. Stauber, R. H. Biotechniques 24(3):462-471 (1998); 3. Heim, R. and Tsien, R. Y. Curr. Biol. 6:178-182 (1996)), enhanced yellow fluorescent protein (EYFP; 1. Clontech Laboratories, Inc., 1020 East Meadow Circle, Palo Alto, Calif. 94303), luciferase (Ichiki et al., J. Immunol. 150(12):5408-5417 (1993)), O-galactosidase (Nolan et al., Proc Natl Acad Sci USA 85(8): 2603-2607 (1988)) and Renilla WO 92/15673; WO 95/07463; WO 98/14605; WO98/26277; WO 99/49019; U.S. Pat. Nos. 5,292,658; 5,418,155; 5,683,888; 5,741,668; 5,777, 079; 5,804,387; 5,874,304; 5,876,995; and 5,925,558). All of the above-cited references are incorporated herein by reference.

Additional labels for use in the present invention include: Alexa-Fluor dyes (Alexa Fluor 350, Alexa Fluor 430, Alexa Fluor 488, Alexa Fluor 546, Alexa Fluor 568, Alexa Fluor 594, Alexa Fluor 633, Alexa Fluor 660, Alexa Fluor 680), Cascade Blue, Cascade Yellow and R-phycoerythrin (PE) (Molecular Probes) (Eugene, Oreg.), FITC, Rhodamine, and Texas Red (Pierce, Rockford, Ill.), Cy5, Cy5.5, Cy7 (Amersham Life Science, Pittsburgh, Pa.). Tandem conjugate protocols for Cy5PE, Cy5.5PE, Cy7PE, Cy5.5APC, Cy7APC are known in the art. Quantitation of fluorescent probe conjugation can be assessed to determine degree of labeling and protocols including dye spectral properties are known in the art.

In another embodiment, the fluorescent label is a GFP and, in at least some embodiments, a renilla, ptilosarcus, or aequorea species of GFP.

In a certain embodiment, a secondary detectable label is used. A secondary label is one that is indirectly detected; for example, a secondary label can bind or react with a primary label for detection, can act on an additional product to generate a primary label (e.g. enzymes), etc. Secondary labels include, but are not limited to, one of a binding partner pair; chemically modifiable moieties; nuclease inhibitors, enzymes such as horseradish peroxidase, alkaline phosphatases, luciferases, etc.

In a certain embodiment, the secondary label is a binding partner pair. For example, the label can be a hapten or antigen, which will bind its binding partner. For example, suitable binding partner pairs include, but are not limited to: antigens (such as proteins (including peptides) and small molecules) and antibodies (including fragments thereof (FAbs, etc.)); proteins and small molecules, including biotin/streptavidin; enzymes and substrates or inhibitors; other protein-protein interacting pairs; receptor-ligands; and carbohydrates and their binding partners. Nucleic acid—nucleic acid binding proteins pairs are also useful. Suitable binding partner pairs include, but are not limited to, biotin (or imino-biotin) and streptavidin, digeoxinin and Abs, and Prolinx™ reagents.

In a certain embodiment, the binding partner pair comprises an antigen and an antibody that will specifically bind to the antigen. By "specifically bind" herein is meant that the partners bind with specificity sufficient to differentiate between the pair and other components or contaminants of the system. The binding should be sufficient to remain bound under the conditions of the assay, including wash steps to remove non-specific binding. In some embodiments, the dissociation constants of the pair will be less than about $10^{-4}$-$10^{-6}$ M$^{-1}$, with less than about $10^{-5}$ to $10^{-9}$ M$^{-1}$ being preferred and less than about $10^{-7}$-$10^{-9}$ M$^{-1}$ being particularly preferred.

In a certain embodiment, the secondary label is a chemically modifiable moiety. In this embodiment, labels comprising reactive functional groups are incorporated into the molecule to be labeled. The functional group can then be subsequently labeled (e.g. either before or after the assay) with a primary label. Suitable functional groups include, but are not limited to, amino groups, carboxy groups, maleimide groups, oxo groups and thiol groups, with amino groups and thiol groups being particularly preferred. For example, primary labels containing amino groups can be attached to secondary labels comprising amino groups, for example using linkers as are known in the art; for example, homo- or heterobifunctional linkers as are well known (see 1994 Pierce Chemical Company catalog, technical section on cross-linkers, pages 155-200, incorporated herein by reference).

In certain embodiments, multiple fluorescent labels are employed with the capture molecules of the present invention. In a preferred embodiment, at least two fluorescent labels are used which are members of a fluorescence resonance energy transfer (FRET) pair.

FRET is a phenomenon known in the art wherein excitation of one fluorescent dye is transferred to another without emission of a photon. A FRET pair consists of a donor fluorophore and an acceptor fluorophore. The fluorescence emission spectrum of the donor and the fluorescence absorption spectrum of the acceptor must overlap, and the two molecules must be in close proximity. The distance between donor and acceptor at which 50% of donors are deactivated (transfer energy to the acceptor) is defined by the Forster radius (Ro), which is typically 10-100 Å. Changes in the fluorescence emission spectrum comprising FRET pairs can be detected, indicating changes in the number of pairs that are in close proximity (i.e., within 100 Å of each other). This will typically result from the binding or dissociation of two molecules, one of which is labeled with a FRET donor and the other of which is labeled with a FRET acceptor, wherein such binding brings the FRET pair in close proximity. Binding of such molecules will result in an increased fluorescence emission of the acceptor and/or quenching of the fluorescence emission of the donor.

FRET pairs (donor/acceptor) useful in the invention include, but are not limited to, EDANS/fluorescien, IAEDANS/fluorescein, fluorescein/tetramethylrhodamine, fluorescein/LC Red 640, fluorescein/Cy 5, fluorescein/Cy 5.5, and fluorescein/LC Red 705.

In another aspect of FRET, a fluorescent donor molecule and a nonfluorescent acceptor molecule ("quencher") can be employed. In this application, fluorescent emission of the donor will increase when quencher is displaced from close proximity to the donor and fluorescent emission will decrease when the quencher is brought into close proximity to the donor. Useful quenchers include, but are not limited to, TAMRA, DABCYL, QSY 7, and QSY 33. Useful fluorescent donor/quencher pairs include, but are not limited to EDANS/DABCYL, Texas Red/DABCYL, BODIPY/DABCYL, Lucifer yellow/DABCYL, coumarin/DABCYL, and fluorescein/QSY 7 dye.

FRET and fluorescence quenching allow for monitoring of binding of labeled molecules over time, providing continuous information regarding the time course of binding reactions.

Changes in the degree of FRET can be determined as a function of the change in the ratio of the amount of fluorescence from the donor and acceptor moieties, a process referred to as "ratioing." Changes in the absolute amount of substrate, excitation intensity, and turbidity or other background absorbance in the sample at the excitation wavelength affect the intensities of fluorescence from both the donor and acceptor approximately in parallel. Therefore, the ratio of the two emission intensities is a more robust and preferred measure of cleavage than either intensity alone.

The ratiometric fluorescent reporter system described herein has significant advantages over existing reporters for protein integration analysis, as it allows sensitive detection and isolation of both expressing and non-expressing single living cells. In a certain embodiment, the assay system uses a non-toxic, non-polar fluorescent substrate which is easily loaded and then trapped intracellularly. Modification of the fluorescent substrate by a cognate protein yields a fluorescent emission shift as substrate is converted to product. Because the reporter readout is ratiometric it is unique among reporter protein assays in that it controls for variables such as the amount of substrate loaded into individual cells. The stable, easily detected, intracellular readout eliminates the need for establishing clonal cell lines prior to expression analysis. This system and other analogous flow sorting systems can be used to isolate cells having a particular receptor element clustering and/or activation profile from pools of millions of viable cells.

Antibody conjugation can be performed using standard procedures (drmr.com.abcon) or by using protein-protein/protein-dye crosslinking kits from Molecular Probes (Eugene, Oreg.). Conjugation of the label moiety to the detection molecule, such as for example an antibody, is a standard manipulative procedure in immunoassay techniques. See, for example, O'Sullivan et al., 1981, "Methods for the Preparation of Enzyme-antibody Conjugates for Use in Enzyme Immunoassay," in Methods in Enzymology, Langone and Van Vunakis, Eds., Vol. 73 (Academic Press, New York, N.Y.), pp. 147-166. Conventional methods are available to bind the label moiety covalently to proteins or polypeptides. For example, coupling agents such as dialdehydes, carbodiimides, dimaleimides, bis-imidates, bis-diazotized benzidine, and the like, can be used to label antibodies with the above-described fluorescent, chemiluminescent, and enzyme labels. See, for example, U.S. Pat. No. 3,940,475 (fluorimetry) and U.S. Pat. No. 3,645,090 (enzymes); Hunter et al., Nature, 144:945 (1962); David et al., Biochemistry, 13:1014-1021 (1974); Pain et al., J. Immunol Methods, 40:219-230 (1981); and Nygren J., Histochem. and Cytochem., 30:407-412 (1982). Fluorescent or chemiluminescent labels can be used to increase amplification and sensitivity to about 5-10 pg/ml, or better.

In the embodiments of the invention the capture molecules are activation specific. The methods and compositions of the present invention can be used to detect any particular receptor element isoform in a sample that is antigenically detectable and antigenically distinguishable from other isoforms of the receptor element which are present in the sample. For example, as demonstrated (see, e.g., the Examples) and described herein, the activation state-specific capture molecules of the present invention can be used in the present methods to identify distinct signaling cascades of a subset or subpopulation of complex cell populations; and the ordering of protein activation (e.g., kinase activation) in potential signaling hierarchies. Further, in the methods of the present invention, the use of flow cytometry, particularly polychromatic flow cytometry, permits the multi-dimensional analysis and functional assessment of the signaling pathway in single cells.

As used herein, the terms "activation state-specific capture molecule" or "activation state molecule", or their grammatical equivalents refer to a capture molecule (i.e., an antibody) that specifically binds to a corresponding and specific antigen. In certain embodiments, the corresponding and specific antigen is a specific isoform of an activatable receptor element. Also preferably, the binding of the activation state-specific antibody is indicative of a specific activation state of a specific activatable receptor element.

In certain embodiments, the binding of an activation state-specific capture molecule to a corresponding isoform of an activatable receptor element is indicative of the identity of the activatable receptor element and of the activation state of the activatable receptor element.

In a certain embodiment, the activation state-specific capture molecule is a peptide comprising a recognition structure that binds to a target structure on an activatable receptor element. A variety of recognition structures are well known in the art and can be made using methods known in the art, including by phage display libraries (see e.g., Gururaja et al., Chem. Biol. (2000) 7:515-27; Houimel et al., Eur. J. Immunol. (2001) 31:3535-45; Cochran et al., J. Am. Chem. Soc. (2001) 123:625-32; Houimel et al., Int. J. Cancer (2001) 92:748-55, each incorporated herein by reference). In a certain embodiment, the activation state-specific capture molecule comprises the following recognition structure: SKVILFE—random peptide loop—SKVILFE. Capture molecules having such recognition structures can bind with high affinity to specific target structures. Further, fluorophores can be attached to such capture molecules for use in the methods of the present invention.

A variety of recognitions structures are known in the art (e.g., Cochran et al., J. Am. Chem. Soc. (2001) 123:625-32; Boer et al., Blood (2002) 100:467-73, each expressly incorporated herein by reference) and can be produced using methods known in the art (see e.g., Boer et al., Blood (2002) 100:467-73; Gualillo et al., Mol. Cell. Endocrinol. (2002) 190:83-9, each expressly incorporated herein by reference), including for example combinatorial chemistry methods for producing recognition structures such as polymers with affinity for a target structure on an activatable protein (see e.g., Barn et al., J. Comb. Chem. (2001) 3:534-41; Ju et al., Biotechnol. (1999) 64:232-9, each expressly incorporated herein by reference). In another embodiment, the activation state-specific capture molecule is a protein that only binds to an isoform of a specific activatable receptor element that is phosphorylated and does not bind to the isoform of this activatable receptor element when it is not phosphorylated or nonphosphorylated. In another embodiment the activation state-specific capture molecule is a protein that only binds to an isoform of an activatable receptor element that is intracellular and not extracellular, or vice versa.

Antibodies, many of which are commercially available have been produced which specifically bind to the phosphorylated isoform of a protein but do not specifically bind to a non-phosphorylated isoform of a protein. Many such antibodies have been produced for the study of signal transducing proteins which are reversibly phosphorylated. Particularly, many such antibodies have been produced which specifically bind to phosphorylated, activated isoforms of protein kinases and are sometimes referred to herein as kinase activation state antibodies or grammatical equivalents thereof. In certain embodiments, antibodies for use in the present invention include: antibodies against phospho-p44/42 MAP kinase (Thr202/Tyr204), phospho-TYK2 (Tyr1054/1055), phospho-p38 MAP kinase (Thr180/Tyr182), phospho-PKC-PAN substrate, pho spho-PKA-sub state, phospho-SAPK/JNK (Thr183/Tyr185), phospho-tyrosine (P-tyr-100), p44/42 MAPK, phospho-MEK1/2 (Ser217/221), phospho-p90RSK (Ser381), p38 MAPK, JNK/SAPK, phospho-Raft (Ser259), phosphoElk-1 (Ser383), phospho-CREB (Ser133), phospho-SEK1/MKK4 (Thr261), phospho-Jun (Ser 63), phospho-MKK3/MKK6 (Ser189/207), AKT, phospho FKHR, FKHR, phospho-Gsk3 alp21, pAFX, PARP, BAD, BADser 112, BADser 136, phospho-BADser 155, p2'7, p21, cFLIP, anti-MYC, p53, NFKB, Ikkα, Ikkβ, phospho-tyrosine and phospho-threonine combination. In certain embodiments of the present invention, these antibodies are monoclonal antibodies. In certain embodiments these antibodies are used in various combinations.

Non-activation state capture molecules, i.e., control capture molecules, can also be used in the present invention. In a certain embodiment, non-activation state capture molecules bind to epitopes in both activated and non-activated forms of a signal transduction pathway protein. Such capture molecules can be used to determine the amount of non-activated plus activated signal transduction pathway protein in a sample. In another embodiment, non-activation state capture molecules bind to epitopes present in non-activated forms of a receptor but absent in activated forms of a signal transduction pathway protein. Such capture molecules can be used to determine the amount of non-activated receptor in a sample. Both types of non-activation state capture molecules can be used to determine if a change in the amount of activation state receptor, for example from samples before and after treatment with a candidate bioactive agent coincide with changes in the amount of non-activation state receptor. For example, such capture molecules can be used to determine whether an increase in activated signal transduction pathway protein is due to activation of a non-activation state signal transduction pathway protein, or due to increased expression of the protein, or both. In other embodiments, the control capture molecule binds to an epitope of the activatable cell that is unaffected by the signaling transduction pathway activation.

The use of control capture molecules is further exemplified in co-pending U.S. application Ser. No. 11/276,948, which is herein incorporated by reference. Preferably, the control capture molecule binds to the same cell that the activation-state specific capture molecule binds, albeit at an epitope that is unactivated by the pan-kinase activator. Thus for example, in certain embodiments of the present invention, the pan-kinase activator activates signal transduction pathways on monocytes. The activation-state specific antibodies detect the activation of the signaling pathways in the monocyte. CD14, which is non-responsive to the pan-kinase activator, could then be used as the target for the control capture molecules. The assay would then be able to detect the monocytes in the sample and which of them have been activated. It is understood that the control capture molecule could bind to a different cell in at least certain embodiments. Thus, by way of example, when monitoring monocyte activation, anti-lymphocyte specific capture molecules could be used as the control capture molecule.

In most embodiments, the control capture molecules is added to the "same tube" as the activation state specific capture molecules. By same tube, it is understood that it is the same reaction container, be that a container, a tube, or a well in a microtiter plate or the like. The control capture molecule thus differs from the traditional isotype controls in that it provides a truer valuation of the base line fluorescence of the test cell. For example, in those embodiments where the cell being evaluated is a monocyte, the control capture molecule can bind to CD14, which is an activation independent monocyte marker. This will permit the setting of the baseline fluorescence of the monocyte population. When those cells are then activated and fluorescence shifts, the degree of shift is accordingly a truer measure of the increase in fluorescence. The use of these controls therefore provide a better way to reduce the background fluorescence of the cells being evaluated. Since phosphorylation states of proteins have been traditionally difficult to identify, let alone quantitate, controlling the background is important to the overall sensitivity of the methods of the present invention.

Thus, in at least certain embodiments, the shift in fluorescence intensity observed through the present invention is generally a 10 fold or greater increase in mean fluorescence intensity. In other embodiments the shift in fluorescence intensity is 20 fold or greater, 30 fold or greater, and even 50 to 100 fold or greater increase in fluorescence intensity.

Immunoassay

Assay systems utilizing a capture molecule and a fluorescent label to quantify captured molecules are well known. Examples of immunoassays useful in the invention include, but are not limited to, fluoroluminescence assay (FLA), chemiluminescence assay (CA), enzyme-linked immunosorbant assay (ELISA) and the like. See, for example, Johnstone and Thorpe, 1996, In: Blackwell, Immunochemistry in Practice, 3rd ed. (Blackwell Publishing, Malden, Mass.); Ausbul et al., eds., 2003, Current Protocols in Molecular Biology, Wiley & Sons (Hoboken, N.J.); Ghindilis et al., eds., 2003, Immunoassay Methods and Protocols, (Blackwell Publishing, Malden, Mass.); and U.S. Patent Publication No. 20030044865. The immunoassay can be a solid phase assay, a liquid phase assay, and the like.

The immunoassay, in one embodiment, can be designed for an automated, high-throughput instrument. For example, the Access® family of instruments by Beckman Coulter, Inc. are well suited to effectuate the methods of the invention. The Access® Immunoassay System allows for rapid throughput of up to 100 tests per hour through the use of a reaction vessel loader that has the capacity for up to 3 hours of continuous sample processing.

In a certain embodiment, flow cytometry is used to detect fluorescence. Other methods of detecting fluorescence can also be used, e.g., Quantum dot methods (see, e.g., Goldman et al., J. Am. Chem. Soc. (2002) 124:6378-82; Pathak et al., J. Am. Chem. Soc. (2001) 123:4103-4; and Remade et al., Proc. Natl. Sci. USA (2000) 18:553-8, each incorporated herein by reference).

For a solid-phase immunoassay, the capture molecule (e.g. a mAb) is immobilized to a solid support. Immobilization conventionally is accomplished by insolubilizing the capture molecule either before the assay procedure, as by adsorption to a water-insoluble matrix or surface (U.S. Pat. No. 3,720,760) or as by non-covalent or covalent coupling (for example, using glutaraldehyde or carbodiimide cross-linking, with or without prior activation of the support with, e.g., nitric acid and a reducing agent as described in U.S. Pat. No. 3,645,852 or in Rotmans et al.; J. Immunol. Methods, 57:87-98 (1983)), or afterward, e.g., by immunoprecipitation.

The solid phase used for immobilization can be any inert support or carrier that is essentially water insoluble and useful in immunometric assays, including supports in the form of, e.g., surfaces, particles, porous matrices, etc. Examples of commonly used supports include small sheets, SEPHADEX® gels, polyvinyl chloride, plastic beads, and assay plates or test tubes manufactured from polyethylene, polypropylene, polystyrene, and the like, including 96-well microtiter plates, as well as particulate materials such as filter paper, agarose, cross-linked dextran, and other polysaccharides. Capture molecules can also be immobilized on a substrate, such as a polymeric bead, colloidal metal or iron oxide particle. Beads can be plastic, glass, or any other suitable material, typically in the 1-20 micron range. In some embodiments, paramagnetic beads are used. Colloidal metal particles such as colloidal gold and silver particles and iron oxide particles can be prepared using many different procedures commercially available or otherwise known to those skilled in the art.

Alternatively, reactive water-insoluble matrices such as cyanogen-bromide-activated carbohydrates and the reactive substrates described in U.S. Pat. Nos. 3,969,287; 3,691,016; 4,195,128; 4,247,642; 4,229,537; and 4,330,440 can be used for capture molecule immobilization. In one embodiment, the immobilized capture molecules are coated on a microtiter plate, and in another embodiment the solid phase is a multiwell microtiter plate that can analyze several samples at one time.

The solid phase is coated with the capture molecules as defined above, which can be linked by a non-covalent or covalent interaction or physical linkage as desired. Techniques for attachment include those described in U.S. Pat. No. 4,376,110 and the references cited therein. If covalent, the plate or other solid phase is incubated with a cross-linking agent together with the capture molecules under conditions well known in the literature.

Commonly used cross-linking agents for attaching the capture molecules to the solid-phase substrate include, e.g., 1,1-bis(diazoacetyl)-2-phenylethane, glutaraldehyde, N-hydroxysuccinimide esters, for example, esters with 4-azidosalicylic acid, homobifunctional imidoesters, including disuccinimidyl esters such as 3,3'-dithiobis(succinimidylpropionate), and bifunctional maleimides such as bis-N-maleimido-1,8-octane. Derivatizing agents such as methyl-3-((p-azidophenyl)-dithio)propioimidate yield photoactivatable intermediates capable of forming cross-links in the presence of light.

The coated plates are then typically treated with a blocking agent that binds non-specifically with and saturates the unoccupied binding sites to prevent unwanted binding of the free ligand to the excess sites on the wells of the plate. Examples of appropriate blocking agents for this purpose include, e.g., gelatin, bovine serum albumin, egg albumin, casein, and non-fat milk. The blocking treatment typically takes place under conditions of ambient temperatures for about 1-4 hours, typically about 1.5 to 3 hours.

The amount of capture molecule employed is sufficiently large to give a good signal in comparison with the calibration standards, but is generally not in molar excess compared to the maximum expected level of signal transduction pathway protein that is of interest in the sample. For sufficient sensitivity, the amount of test sample should be added such that the immobilized capture molecules are in molar excess of the maximum molar concentration of free analyte of interest anticipated in the test sample after appropriate dilution of the sample.

Generally, the conditions for incubation of sample and immobilized capture molecule are selected to maximize analytical sensitivity of the assay to minimize dissociation, and to ensure that sufficient analyte of interest that is present in the sample binds with the immobilized capture molecule. It is understood that the selection of optimum reaction conditions generally requires only routine experimentation. The incubation is accomplished at fairly constant temperatures, ranging from about 0° C. to about 40° C., generally at or about room temperature. The time for incubation is generally no greater than about 10 hours. The duration of incubation can be longer if a protease inhibitor is added to prevent proteases in the test sample from degrading the signal transduction pathway proteins of interest.

Methods of the Present Invention

The present invention provides methods for determining the activation state of a signal transduction pathway protein in a sample which comprises contacting the unmasked intracellular epitopes of the preserved leukocytes in the sample with a plurality of fluorescently labeled capture molecules, the plurality of capture molecules comprise at least two different capture molecules capable of binding to the activated state of the at least two different unmasked intracellular epitopes of the preserved, activated leukocytes in the sample. In this embodiment, the preserved, activated leukocytes captured by the capture molecule are detected using one of the immunoassay formats described above. In certain embodiments, the fluorescence detection detects the labeled capture molecules bound to the activated state of the unmasked intracellular epitopes. The preserved leukocytes are similarly detected. Therefore in certain embodiments, the immunoassay detects fluorescence of the preserved leukocyte captured by the binding of the control capture molecule.

When using fluorescent labeled components in the methods and compositions of the present invention, it will recognized that different types of fluorescent monitoring systems, e.g., flow cytometry systems, can be used to practice the invention. In some embodiments, flow cytometry systems are used or systems dedicated to high throughput screening, e.g. 96-well or greater microtiter plates. Methods of performing assays on fluorescent materials are well known in the art and are described in, e.g., Lakowicz, J. R., Principles of Fluorescence Spectroscopy, New York: Plenum Press (1983); Herman, B., Resonance energy transfer microscopy, in: Fluorescence Microscopy of Living Cells in Culture, Part B, Methods in Cell Biology, vol. 30, ed. Taylor, D. L. & Wang, Y.-L., San Diego: Academic Press (1989), pp. 219-243; Turro, N.J., Modern Molecular Photochemistry, Menlo Park: Benjamin/Cummings Publishing Col, Inc. (1978), pp. 296-361.

Fluorescence in a sample can be measured using a fluorimeter. In general, excitation radiation, from an excitation source having a first wavelength, passes through excitation optics. The excitation optics cause the excitation radiation to excite the sample. In response, fluorescent proteins in the sample emit radiation which has a wavelength that is different from the excitation wavelength. Collection optics then collect the emission from the sample. The device can include a temperature controller to maintain the sample at a specific temperature while it is being scanned. According to one embodiment, a multi-axis translation stage moves a microtiter plate holding a plurality of samples in order to position different wells to be exposed. The multi-axis translation stage, temperature controller, auto-focusing feature, and electronics associated with imaging and data collection can be managed by an appropriately programmed digital computer. The computer also can transform the data collected during the assay into another format for presentation.

In another embodiment, capture molecules, such as antibodies, are immobilized using beads analogous to those known and used for standardization in flow cytometry. Attachment of a multiplicity of activation state specific capture molecules to beads can be done by methods known in the art and/or described herein. Such conjugated beads can be contacted with a sample, preferably a cell extract, under conditions which allow for a multiplicity of activated receptor elements, if present, to bind to the multiplicity of immobilized capture molecules. A second multiplicity of capture molecules comprising non-activation state capture molecules which are uniquely labeled can be added to the immobilized activation state specific antibody-activated receptor complex and the beads can be sorted by flow cytometry on the basis of the presence of each label, wherein the presence of label indicates binding of corresponding second capture molecule and the presence of corresponding activated receptor.

Once the fluorescence of the activated-state specific capture molecules and control capture molecules have been detected, their fluorescence can be compared. The terms "correlate" or "compare", or their grammatical equivalents, are intended to be used interchangeably, unless the particular context connotes a different meaning. Correlating/comparing is meant comparing, in any way, the performance and/or results of a first analysis with the performance and/or results of a second analysis. For example, as described in greater detail below, the level of MAPK activity in a sample that had been subjected to MAPK inhibitor differs from the level of MAPK activity in a sample that has not been subjected to the same inhibitor. By identifying a particular activity level, the MAPK protein's activity can act as an indicator or as a predictor of prognosis for a specific disease condition, thereby "correlating" activity with disease condition status. In the diseases and conditions discussed elsewhere herein in, the disease or condition can be characterized by a lack of an activation response when exposed to the pan-kinase activator. Similarly, as described elsewhere herein the responsiveness of the disease or condition to treatment can be identified by evaluating the fluorescence of the various capture molecules to identify the re-emergence of a pan-kinase activation response.

In other embodiments, the fluorescence of the activated signal transduction pathway protein can be evaluated against the fluorescence of an unactivated signal transduction pathway protein. The purpose in these evaluations is to discern whether a difference exists between the fluorescence signal generated by the activated vs. unactivated or the activated vs. standardized reference sample. Generally, these evaluations constitute a second correlation step. In at least some embodiments, the unactivated reference sample is a second aliquot of the sample.

The standardized reference sample is, in one embodiment, a manufacturer-set value of expected fluorescence of an unactivated cell sample treated under highly reproducible conditions. These types of standardized reference values are intended to serve as surrogates to the values that the end user would achieve were they to run a parallel unactivated sample. A purpose of these standardized reference values is to achieve efficiency in labor for the end user in that the end user would not need to run a parallel sample, and the labor and reagent costs associated with preparing and running such a parallel sample. Manufacturers of diagnostic reagent kits, such as Beckman Coulter, are well accustomed to preparing standardized reference values for their reagents and kits.

The immunoassay of the present invention provides a higher degree of specificity than the present assays described in the art. Specificity is provided through the use of vigorous controls. Specifically, in the prior art, the percent cells positive for a particular marker(s) was measured in a specific cell. Generally, the cells were stained using an antibody isotype control. The signal from the MAPK pathway proteins, for example, would then be measured and reported as the activity minus the background signal. Since the strength of many signals is low, as well as transient in nature, the high background levels do not allow for application of the assays in a clinical setting. In the present invention, intracellular epitopes for the proteins are unmasked using the detergent and alcohol treatments. Specificity is then obtained using internal standards and composite profiles of various activities. In one embodiment, monocytes are identified by flow cytometry using side and forward scatter coupled with expression of the cell surface marker CD14. In a further embodiment, the activity of the MAPK proteins is measured in unstimulated vs. stimulated with LPS. This activity can be reported as an activity ratio of stimulated over unstimlated cells, or, a signal to noise (S/N) ratio. This ratio provides a true baseline measurement and aids in reducing the unacceptably high background levels of the prior art assays.

As previously indicated, a S/N ratio of greater than about 10 can be achieved through the use of the methods of the present invention. In other embodiments, a S/N ratio of greater than about 20, greater than about 30, and even greater than about 50 can be achieved through the application of the methods described herein.

It is understood that in most embodiments of the present invention that the S/N ratios may vary depending on the signaling pathway protein being evaluated. Thus, some signaling pathway proteins inherently yield greater noise than others. Thus, in certain embodiments, a first signaling pathway protein achieves, for example, a S/N ratio of about 10 and a second signaling pathway protein achieves, for example, a S/N ratio of about 20.

As exemplified above, certain cancers or diseases are characterized by the systemic activation of the signal transduction pathway signaling proteins. When these abnormal samples are characterized by the methods of the present invention, the assay is unable to discern a difference in fluorescence between the naive sample and the sample that has been activated by the pan-kinase activator. Indeed, the signal transduction pathway signaling proteins are already under a state of activation.

In certain embodiments, the invention relates to methods of monitoring the activity of signal transduction pathway protein inhibitors which have been administered to patients. When these patients are receiving a signal transduction pathway protein inhibitor, the inhibitor shuts down or reduces the activation state of the signal transduction pathway proteins. Normally, these inhibitors titrate from the patient or test sample over time and are re-administered to maintain their effectiveness/efficacy. At a time just prior to the re-administration of the inhibitor, a patient sample (or in the case of a tissue culture assay—a cell sample) can be obtained and the leukocytes in that sample can be tested using the assays of the present invention. If the inhibitor is being effective to treat the disease or condition, the assay will reveal the re-emergence of the pan-kinase response observed in a normal, i.e., non-diseased, sample. Thus, the present invention, in at least one embodiment, provides a highly effective, sensitive blood assay to monitor the progression of the clinical treatment of diseases or conditions characterized by an aberrant signal transduction pathway protein activation.

It is understood that certain signal transduction associated diseases or conditions include inflammation, fever, sepsis, cancer, diabetes, and heart failure. In preferred embodiments of the present invention the condition is sepsis.

When a patient has sepsis, the bacteria causing the sepsis condition secrete endotoxins that lead to the over-stimulation of signal transduction pathway proteins. This over-stimulation leads in some cases to patient death. In the embodiment of the present invention pertaining to sepsis detection and/or monitoring, the sepsis patient sample will not respond to the pan-kinase activator following the protocols generally outlined in the present invention. Thus, in at least one embodiment of the present invention, sepsis can be detected by monitoring for a non-response to pan-kinase activation.

Sepsis is generally treated by administering antibiotic agents to the septic patient. As a way to monitor the clinical progress of the septic patient, the assays of the present invention can be used to monitor for the re-occurrence of the pan-kinase activation response. Thus, for a septic patient that previously showed no significant signal transduction pathway protein activation by the pan-kinase activator, it is understood that the antibiotic regimen is beginning to treat the underlying sepsis when the patient sample begins to demonstrate the signal transduction pathway protein activation by the pan-kinase activator.

In at least certain embodiments, the method comprises simultaneously determining the presence of activated isoforms of a multiplicity of signal transduction pathway proteins using a multiplicity of antibodies that specifically bind to active, phosphorylated isoforms of the multiplicity of receptor elements.

Additional ways for determining kinase activation are provided by the present invention. Substrates that are specifically recognized by protein kinases and phosphorylated thereby are known. Antibodies that specifically bind to such phosphorylated substrates but do not bind to such non-phosphorylated substrates (phospho-substrate antibodies) can be used to determine the presence of activated kinase in a sample.

Using certain embodiments of the invention, altered levels of activity of signal transduction pathway proteins can be associated with the prognosis of many diseases or conditions including, but not limited to, allergic, inflammatory, autoimmune or neoplastic conditions.

In a certain embodiment, the present invention provides methods for determining a signal transduction pathway protein's activation state profile for a single cell. The methods comprise sorting cells by flow cytometry on the basis of the activation state of at least two signal transduction pathway proteins. Activation state-specific antibodies are used to sort cells on the basis of signal transduction pathway protein activation state.

In a certain embodiment, methods for the determination of a signal transduction pathway protein activation state profile for a single cell are provided. The methods comprise providing a population of cells and sorting the population of cells by flow cytometry. In certain embodiments, cells are separated on the basis of the activation state of at least two signal transduction pathway proteins. In a certain embodiment, a multiplicity of signal transduction pathway protein activation state antibodies are used to simultaneously determine the activation state of a multiplicity of signal transduction pathway proteins.

In a certain embodiment, cell sorting by flow cytometry on the basis of the activation state of at least two signal transduction pathway proteins is combined with a determination of other flow cytometry readable outputs, such as the presence of surface markers, granularity and cell size to provide a correlation between the activation state of a multiplicity of receptor elements and other cell qualities measurable by flow cytometry for single cells. In certain embodiments, the presence of the cell surface marker CD14 is used to identify monocyte populations.

The present invention can also be used to determine the presence of cellular subsets, based on correlated receptor element activation within complex cellular mixtures such as peripheral blood mononuclear cells. These subsets can represent different differentiation or activation states or different cell lineages or sublineages.

It will also be recognized that a homogeneous cell population is desirable for studying signal transduction in order that variances in signaling between cells not qualitatively and quantitatively mask signal transduction events. The ultimate homogeneous system is the single cell. The present invention provides methods for the analysis of signal transduction in single cells, where the activated state of the signal transducing receptor element involved is antigenically distinguishable from a non-activated state.

These methods also provide for the identification of distinct signaling cascades for both artificial and stimulatory conditions in complex cell populations, such as peripheral blood mononuclear cells, or naive and memory lymphocytes.

The methods provided herein can also involve the use of specific inhibitors of particular receptor elements. The methods provided herein can also involve the use of other pharmacological inhibitors of signaling pathways. These inhibitors can be used as controls to ensure that antibodies specifically bind to activated isoforms of receptor elements. For example, an inhibitor of a signal transduction pathway protein known to phosphorylate and activate a kinase can be used to inhibit phosphorylation of the kinase and examine whether an antibody specifically recognizes a phosphorylated isoform of the kinase. Alternatively, the inhibitors can be used to further probe signaling pathways and correlations in protein activity, particularly in single cells.

In certain embodiments, signal transduction pathway protein activity is determined using two or more activation state specific antibodies. In embodiments where two or more antibodies are used, the antibodies are uniquely labeled, meaning that a first activation state antibody recognizing a first signal transduction pathway protein comprises a first label, and second activation state antibody recognizing a second signal transduction pathway protein comprises a second label, wherein the first and second label are detectable and distinguishable, making the first antibody and the second antibody uniquely labeled. The use of a second signal transduction pathway protein serves as an internal control to confirm specificity of the measured activity.

In certain embodiments, signal transduction pathway protein activity is determined using three or more activation state specific capture molecules, including specifically monoclonal antibodies. In embodiments where three or more capture molecules are used, the antibodies are uniquely labeled, meaning that a first activation state capture molecule recognizing a first signal transduction pathway protein comprises a first label, a second activation state capture molecule recognizing a second signal transduction pathway protein comprises a second label, and a third activation state capture molecule recognizing a third signal transduction pathway protein comprises a third label, wherein the first, second, and third labels are detectable and distinguishable, making the first capture molecule, the second capture molecule, and the third capture molecules uniquely labeled.

It is understood that in evaluating more than one, preferably more than two, and in some embodiments more than three different signal transduction pathway proteins, the methods of the present invention provide for a greater degree of sensitivity to the activation response of a cell to a pan-kinase activator. Cell signaling pathways are complex systems and employing multiple capture molecules to capture the activation states of multiple pathway proteins permits the user to design systems to accurately measure and monitor the activation state of these signaling pathways, including specifically their response to treatment regimens designed to control the activation state of the signaling proteins. For example, in the context of the LPS activation experiments described below, certain signaling proteins responded differently over time to the LPS activation. Thus by monitoring a panel of activation state proteins, the system can much more reliably assess the activation state of a cell in response to a disease or condition and thus the activation state of such cells that are being treated for that disease or condition.

Although exemplified herein with regard to intracellular phospho-proteins/epitopes, the methods of the invention are equally applicable for preparation of samples aimed at measuring other post-translational modifications including, for example, ubiquitination, glycosylation, methylation, acetylation, palmitolyation, or protein-protein interactions. Thus, the invention enables the detection of non-phospho epitopes of a variety of proteins within cells, expanding the utility of the methods further. Labeled binding agents can be selected based on the particular cellular events to be studied. The methods provided by the invention allow for the examination of pathways in detailed time courses and pathway-specific manners that have previously not been available. Although diverse intracellular epitopes can be selected for flow cytometric analysis, it is understood that the user can optimize and tailor the method provided herein for the specific epitope in question by taking into account factors including, for example, localization, conformation/structure, accessibility by antibodies, and stability of the epitope. The methods provided herein are generally applicable to multicolor, multiparameter cytometry analysis.

In another embodiment, control cells are not stimulated with LPS. These unstimulated cells are used to provide a ratio of the level of signal between stimulated and unstimulated cells. In one embodiment, the ratio is the difference in mean fluorescent intensity between LPS stimulated and unstimulated cells. In another embodiment, the control cells are unstimulated monocytes. In a further embodiment, the ratio is the difference in mean fluorescent intensity between LPS stimulated monocytes versus unstimulated monocytes. Using vigorous internal controls, differences in the activity of the MAPK proteins are readily visible which allows for the correlation between activity and a particular disease condition.

Test Compounds

Candidate agents are obtained from a wide variety of sources, as will be appreciated by those in the art, including libraries of synthetic or natural compounds. As will be appreciated by those in the art, the present invention provides a rapid and easy method for screening any library of candidate modulators, including the wide variety of known combinatorial chemistry-type libraries.

In a certain embodiment, a method for screening for a bioactive agent capable of inhibiting signal transduction pathway protein activity is provided which comprises contacting a cell with a putative bioactive agent and determining signal transduction pathway protein activation in said cell by flow cytometry.

By "putative agent", "putative inhibitor", "putative therapeutic agent", or "putative signal transduction pathway inhibitor" is meant any molecule, e.g., protein, small organic molecule, carbohydrates (including polysaccharides), polynucleotide, lipids, etc. that is being evaluated for its ability to affect the signaling of a signal transduction pathway protein.

Generally a plurality of assay mixtures can be run in parallel with different agent concentrations to obtain a differential response to the various concentrations. Typically, one of these concentrations can serve as a negative control, i.e., at zero concentration or below the level of detection. In addition, positive controls can be used.

In at least one embodiment, the effectiveness of a putative kinase inhibitor is measured by exposing a leukocyte-containing sample to the putative kinase inhibitor, activating the activatable proteins of at least one signal transduction pathway in the leukocyte-containing sample by exposing the sample to a pan-kinase activator, preserving the blood sample, and unmasking intracellular epitopes of the preserved leukocytes in the sample. The activation state of the signal transduction pathway proteins in the sample are then determined by contacting the unmasked intracellular epitopes of the preserved leukocytes in the sample with a plurality of detectably labeled capture molecules, the plurality of capture molecules comprise at least two different capture molecules capable of binding to the activated state of the two different unmasked intracellular epitopes of the preserved, activated leukocytes in the blood sample. In this embodiment, the preserved, activated leukocytes are detected using one of the immunoassay formats described above. In certain embodiments, the fluorescence detection detects the labeled capture molecules bound to the activated state of the unmasked intracellular epitopes. The preserved leukocytes are similarly detected. Therefore in certain embodiments, the immunoassay detects fluorescence of the preserved leukocyte captured by the binding of the control capture molecule.

In this embodiment, generally, a parallel sample is processed under the same conditions, but without exposure to the putative kinase inhibitor.

The detected fluorescence of the putative inhibitor exposed cells can then be compared against the detected fluorescence of the naive sample, i.e., the sample that was not exposed to the putative inhibitor. In the case of the naive sample, the pan-kinase activator will activate the available signal transduction pathway proteins and a shift in fluorescence will be observed. However, to the extent the putative inhibitor is effective at affecting signal transduction pathway protein activation, the shift in fluorescence will either be not observed or the shift will be less dramatic than that observed in the control sample. The degree to which the shift in fluorescence is shut down or diminished correlates to the effectiveness of that putative inhibitor.

It is understood that in the embodiment just described, the use of the parallel control sample is optional. Activity of the putative kinase inhibitor can be monitored using appropriate controls in a one-tube assay format.

In at least one embodiment, the present invention provides methods for identifying putative inhibitors that affect ribosomal S6 pathway activation. As shown in Example 1, ribosomal S6 pathway activation requires the inhibition of both the ERK and PI3K signaling proteins. Thus, to the extent that the assay is intended to test putative ERK inhibitor, the sample is exposed to the putative inhibitor and a known PI3K inhibitor, such as LY294002. The putative inhibitor is effective at affecting ERK signaling when it is observed that ribosomal S6 activation has been affected. Similarly, to the extent that the assay is intended to test putative PI3K inhibitor, the sample is exposed to the putative inhibitor and a known ERK inhibitor, such as U0126. The putative inhibitor is effective at affecting PI3K signaling when it is observed that ribosomal S6 activation has been affected.

It is of course understood that ribosomal S6 pathway activation is not the only pathway that requires the inhibition of multiple pathway members in order to shut down the total pathway. Other such examples are known to those in the field and they are intended to be encompassed by the present invention.

Putative agents encompass numerous chemical classes. In a certain embodiment, the candidate agents are small molecules. In another embodiment, the candidate agents are organic molecules, particularly small organic molecules, comprising functional groups necessary for structural interaction with proteins, particularly hydrogen bonding, and typically include at least an amine, carbonyl, hydroxyl or carboxyl group, preferably at least two of the functional chemical groups. The candidate agents often comprise cyclical carbon or heterocyclic structures and/or aromatic or polyaromatic structures substituted with one or more chemical functional groups.

In a certain embodiment, putative agents are synthetic compounds, as described above in connection with signal transduction pathway proteins. One advantage of the present method is that it is not necessary to characterize the putative agent prior to the assay. Using the methods of the present invention, any candidate agents can be screened for the ability to modulate (e.g., increase or decease) the activity of an activatable protein.

Alternatively, a certain embodiment utilizes libraries of natural compounds, as putative agents, in the form of bacterial, fungal, plant and animal extracts that are available or readily produced. Additionally, natural or synthetically produced libraries and compounds are readily modified through conventional chemical, physical and biochemical means. Known pharmacological agents can be subjected to directed or random chemical modifications, including enzymatic modifications, to produce structural analogs.

In a certain embodiment, the putative agents are peptides of from about 2 to about 50 amino acids, with from about 5 to about 30 amino acids being preferred, and from about 8 to about 20 being particularly preferred. The peptides can be digests of naturally occurring proteins as is outlined above, random peptides, or "biased" random peptides. By "randomized" is meant that each nucleic acid and peptide consists of essentially random nucleotides and amino acids, respectively. Since generally these random peptides (or nucleic acids, discussed below) are chemically synthesized, they can incorporate any nucleotide or amino acid at any position. The synthetic process can be designed to generate randomized proteins or nucleic acids, to allow the formation of all or most of the possible combinations over the length of the sequence, thus forming a library of randomized candidate bioactive proteinaceous agents.

The library should provide a sufficiently structurally diverse population of randomized agents to effect a probabilistically sufficient range of diversity to allow interaction with a particular activatable protein. Accordingly, an interaction library must be large enough so that at least one of its members will have a structure that interacts with an activatable protein or other specific components of the signal transduction pathway involving the activatable protein. Although it is difficult to gauge the required absolute size of an interaction library, nature provides a hint with the immune response: a diversity of $10^7$-$10^8$ different antibodies provides at least one combination with sufficient affinity to interact with most potential antigens faced by an organism. Published in vitro selection techniques have also shown that a library size of $10^7$ to $10^8$ is sufficient to find structures with affinity for a target. A library of all combinations of a peptide 7 to 20 amino acids in length, such as generally proposed herein, has the potential to code for $20^7$ ($10^9$) to $20^{20}$. Thus, with libraries of $10^7$ to $10^8$ different molecules the present methods allow a "working" subset of a theoretically complete interaction library for 7 amino acids, and a subset of shapes for the $20^{20}$ library. Thus, in a preferred embodiment, at least $10^6$, preferably at least $10^7$, more preferably at least $10^8$ and most preferably at least $10^9$ different sequences are simultaneously analyzed in the subject methods. Preferred methods maximize library size and diversity.

In one embodiment, the library is fully randomized, with no sequence preferences or constants at any position. In a certain embodiment, the library is biased. That is, some positions within the sequence are either held constant, or are selected from a limited number of possibilities. For example, in a certain embodiment, the nucleotides or amino acid residues are randomized within a defined class, for example, of hydrophobic amino acids, hydrophilic residues, sterically biased (either small or large) residues, towards the creation of cysteines, for cross-linking, prolines for SH-3 domains, serines, threonines, tyrosines, or histidines for phosphorylation sites, etc., or to purines, etc.

In a certain embodiment, the bias is towards peptides or nucleic acids that interact with known classes of molecules. For example, when the candidate agent is a peptide, it is known that much of intracellular signaling is carried out via short regions of proteins interacting with other proteins through small peptide domains. For instance, a short region from the HIV-1 envelope cytoplasmic domain has been previously shown to block the action of cellular calmodulin. Regions of the Fas cytoplasmic domain, which shows homology to the mastoparan toxin from Wasps, can be limited to a short peptide region with death-inducing apoptotic or G protein inducing functions. Magainin, a natural peptide derived from *Xenopus*, can have potent anti-tumor and anti-microbial activity. Short peptide fragments of a protein kinase C isozyme ((PKC), have been shown to block nuclear translocation of βPKC in *Xenopus* oocytes following stimulation. And, short SH-3 target peptides have been used as psuedosubstrates for specific binding to SH-3 proteins. This is of course a short list of available peptides with biological activity, as the literature is dense in this area. Thus, there is much precedent for the potential of small peptides to have activity on intracellular signaling cascades. In addition, antagonists of any number of molecules can be used as the basis of biased randomization of candidate inhibitors as well.

Thus, a number of molecules or protein domains are suitable as starting points for the generation of biased randomized candidate inhibitors. A large number of small molecule domains are known, that confer a common function, structure or affinity. In addition, as is appreciated in the art, areas of weak amino acid homology can have strong structural homology. A number of these molecules, domains, and/or corresponding consensus sequences, are known, including, but are not limited to, SH-2 domains, SH-3 domains, Pleckstrin, death domains, protease cleavage/recognition sites, enzyme inhibitors, enzyme substrates, and Traf.

In a certain embodiment, the putative inhibitor is a polypeptide. In another embodiment, the polypeptide is a cyclic peptide having at least 4 to 20 amino acids. Also in another embodiment, the polypeptide is a catalytically inactive polypeptide. Examples of catalytically inactive polypeptides include, but are not limited to, catalytically inactive activatable proteins and, more specifically a catalytically inactive kinases (e.g., PI3K) or caspases. In a further aspect, the candidate modulating agent is peptide fragment of an activatable protein, wherein the peptide fragment comprises an amino acid sequence that is a subsequence of the full-length amino acid sequence of the activatable protein.

As will be appreciated that it is possible to screen more than one type of candidate agent at a time, e.g., by combining the putative agents in the methods of the present invention. Thus, the library of putative agents used can include only one type of agent (i.e. peptides), or multiple types (peptides and organic agents).

By combining is meant the combining of the various components in a reaction mixture in vitro or in a cell in vivo under conditions which promote an activity that is detectable using known methods or using the methods of the present invention (e.g., the binding of an antibody to a corresponding antigen or isoform of an activatable protein, or activation state of an activatable protein).

The Present Assays are Non-Limiting

It is understood that the steps of the assays provided herein can vary in their order. It is also understood, however, that while various options (of compounds, properties selected or order of steps) are provided herein, the options are also each provided individually, and can each be individually segregated from the other options provided herein. Moreover, steps which are obvious and known in the art that will increase the sensitivity of the assay are intended to be within the scope of this invention. For example, there can be additionally washing steps, blocking steps, etc.

In a certain embodiment, the reaction mixture or cells are contained in a well of a 96-well plate or other commercially available multi-well plate. In an alternate embodiment, the reaction mixture or cells are in a flow cytometry machine. Other multi-well plates useful in the present invention include, but are not limited to 384-well plates and 1536-well plates. Still other vessels for containing the reaction mixture or cells and useful in the present invention will be apparent.

The addition of the components of the assay for detecting the activation state or activity of signal transduction pathway protein, or inhibition of such activation state or activity, can be sequential or in a predetermined order or grouping under conditions appropriate for the activity that is assayed for. Such conditions are described here and known in the art.

In a certain embodiment, the methods of the invention include the use of liquid handling components. The liquid handling systems can include robotic systems comprising any number of components. In addition, any or all of the steps outlined herein can be automated; thus, for example, the systems can be completely or partially automated.

As will be appreciated there are a wide variety of components which can be used, including, but not limited to, one or more robotic arms; plate handlers for the positioning of microplates; automated lid or cap handlers to remove and replace lids for wells on non-cross contamination plates; tip assemblies for sample distribution with disposable tips; washable tip assemblies for sample distribution; 96 well loading blocks; cooled reagent racks; microtiter plate pipette positions (optionally cooled); stacking towers for plates and tips; and computer systems.

Fully robotic or microfluidic systems include automated liquid-, particle-, cell- and organism-handling including high throughput pipetting to perform all steps of screening applications. This includes liquid, particle, cell, and organism manipulations such as aspiration, dispensing, mixing, diluting, washing, accurate volumetric transfers; retrieving, and discarding of pipet tips; and repetitive pipetting of identical volumes for multiple deliveries from a single sample aspiration. These manipulations are cross-contamination-free liquid, particle, cell, and organism transfers. This instrument performs automated replication of microplate samples to filters, membranes, and/or daughter plates, high-density transfers, full-plate serial dilutions, and high capacity operation.

In a certain embodiment, chemically derivatized particles, plates, cartridges, tubes, magnetic particles, or other solid phase matrix with specificity to the assay components are used. The binding surfaces of microplates, tubes or any solid phase matrices include non-polar surfaces, highly polar surfaces, modified dextran coating to promote covalent binding, antibody coating, affinity media to bind fusion proteins or peptides, surface-fixed proteins such as recombinant protein A or G, nucleotide resins or coatings, and other affinity matrix are useful in this invention.

In a certain embodiment, platforms for multi-well plates, multi-tubes, holders, cartridges, mini-tubes, deep-well plates, microfuge tubes, cryovials, square well plates, filters, chips, optic fibers, beads, and other solid-phase matrices or platform with various volumes are accommodated on an upgradable modular platform for additional capacity. This modular platform includes a variable speed orbital shaker, and multi-position work decks for source samples, sample and reagent dilution, assay plates, sample and reagent reservoirs, pipette tips, and an active wash station.

In a certain embodiment, interchangeable pipet heads (single or multi-channel) with single or multiple magnetic probes, affinity probes, or pipetters robotically manipulate the liquid, particles, cells, and organisms. Multi-well or multi-tube magnetic separators or platforms manipulate liquid, particles, cells, and organisms in single or multiple sample formats.

The compounds identified using the disclosed assay are potentially useful as therapeutics for many disease states including allergy, autoimmunity and neoplastic conditions. The amount of such compound(s) will be an amount that yields the desired degree of inhibition of a signal transduction pathway protein can generally be between 0.001 and 10000 µM.

Kits

As a matter of convenience, the method of this invention can be provided in the form of a kit. Such a kit is a packaged combination comprising the basic elements of: (a) a pan kinase activator; (b) at least one capture molecule that binds at least one signal transduction pathway protein; and (c) instructions on how to perform the method using these reagents. In certain embodiments, the kit contains at least two capture molecules that binds at least two signal transduction pathway proteins. In certain embodiments, the kit contains at least three capture molecules that binds at least three signal transduction pathway proteins.

In one embodiment, the kit can further provide inhibitors of a signal transduction pathway protein. These inhibitors are useful to confirm that the signal transduction pathway protein inhibitor is specific to its target protein and does not generally inhibit multiple functions within the cell. In certain embodiments, the signal transduction pathway inhibitor is a MAPK pathway protein inhibitor. Several MAPK pathway protein inhibitors are commercially available and include, but are not limited to U0126, Ly294002, AZD6244, PD0325901, XL518, hypothemycin, anthrax lethal factor, RAF265, PLX4032, XL281, Bay 43-9006, and Zarnestra.

In another embodiment, the kit further comprises a solid support for the capture molecules, which can be provided as a separate element or as an element on which the capture molecules are already immobilized. Hence, the capture molecules in the kit either can be immobilized already on a solid support, or can become immobilized on a support that is included with the kit or provided separately from the kit. Where the capture molecule is labeled with an enzyme, the kit will ordinarily include substrates and cofactors required by the enzyme, where the label is a fluorophore, a dye precursor that provides the detectable chromophore, and where the label is biotin, an avidin such as avidin, streptavidin, either alone or conjugated to a chromophore.

The kit can further include an instruction sheet, describing how to carry out the assay of the kit.

EXAMPLES

Example 1

Protocol for LPS Activation of MAPK Signaling in Whole Blood Samples

100 µl of blood was inserted into the bottom of 12×75 mm tubes. Blood was removed from the side of tube with cotton swab to eliminate potential contamination of the sample with unfixed cells. 100 ng lipopolysaccharide (LPS) was added to activation tubes (or equal volume of phosphate buffered saline (PBS) to control tubes) and the tubes were placed in 37° C. water bath.

After various incubation times (e.g. 1 minute to 60 minutes), the first tube was removed from the incubator and 65 µl 10% formaldehyde was added into tube. The tubes were mixed and placed in a rack and incubated at room temperature. After exactly a 10 minute incubation with formaldehyde, 1 ml Lyse/Permeabilization Buffer (585 µl TRITON X-100 10% stock solution to 500 ml with PBS. 0.1165% TRITON X-100 solution at room temperature in the dark and pre-heated to 37° C. immediately prior to use.) was added to each tube, vortexed vigorously and returned to the rack. The tubes were incubated at room temperature for 15 minutes.

2 ml cold Wash Buffer (PBS (w/o Ca++/Mg++) with 4% FBS, sterile filtered (0.22 um filter)) (4° C.) was added to each tube. All tubes were centrifuged at 500×g for 4 minutes. Tubes were removed from the centrifuge and supernate fluid was aspirated. 1 ml of cold (4° C.) 50% methanol was added to each tube and vortexed. All tubes were then incubated on ice for 10 minutes.

The tubes were then centrifuged at 500×g for 4 minutes and the supernate fluid was aspirated. 2 ml cold Wash Buffer (4° C.) was added to each tube. All tubes were centrifuged at 500×g for 4 minutes. Tubes were removed from the centrifuge and supernate fluid was aspirated.

Antibodies and cold Wash Buffer were added to a final volume of 100 µl and incubated at room temperature for 30 minutes. 2 ml cold Wash buffer was added, mixed and centrifuged. Cells were resuspended in 1 ml Wash Buffer, vortexed and analyzed on the flow cytometer.

Figure 2:
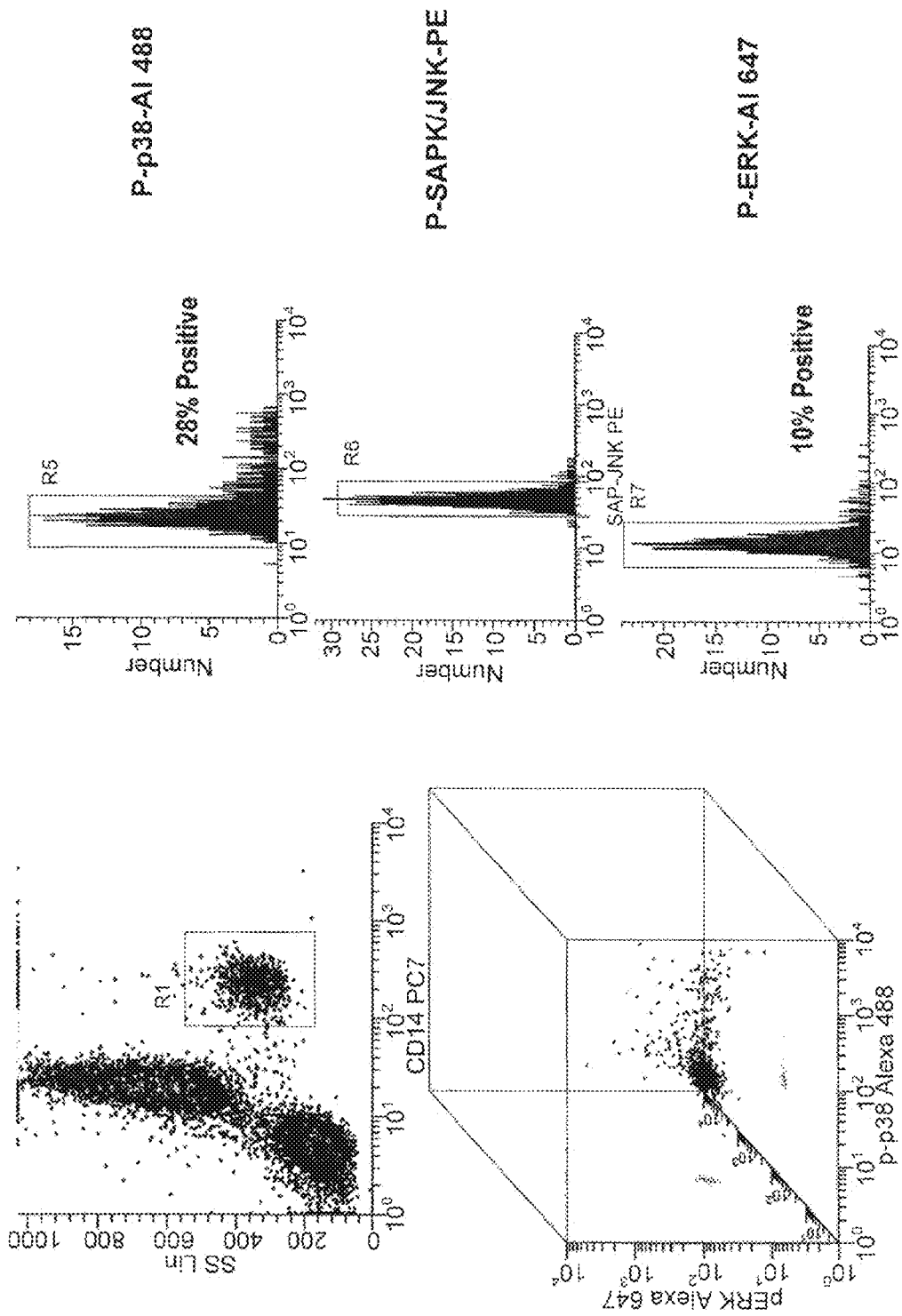
FIG. 2 shows the simultaneous measurement of 3 MAPK pathway members (p38, JNK, and ERK) in unstimulated whole blood. CD14 was used to identify monocytes in whole blood samples.
Figure 3:
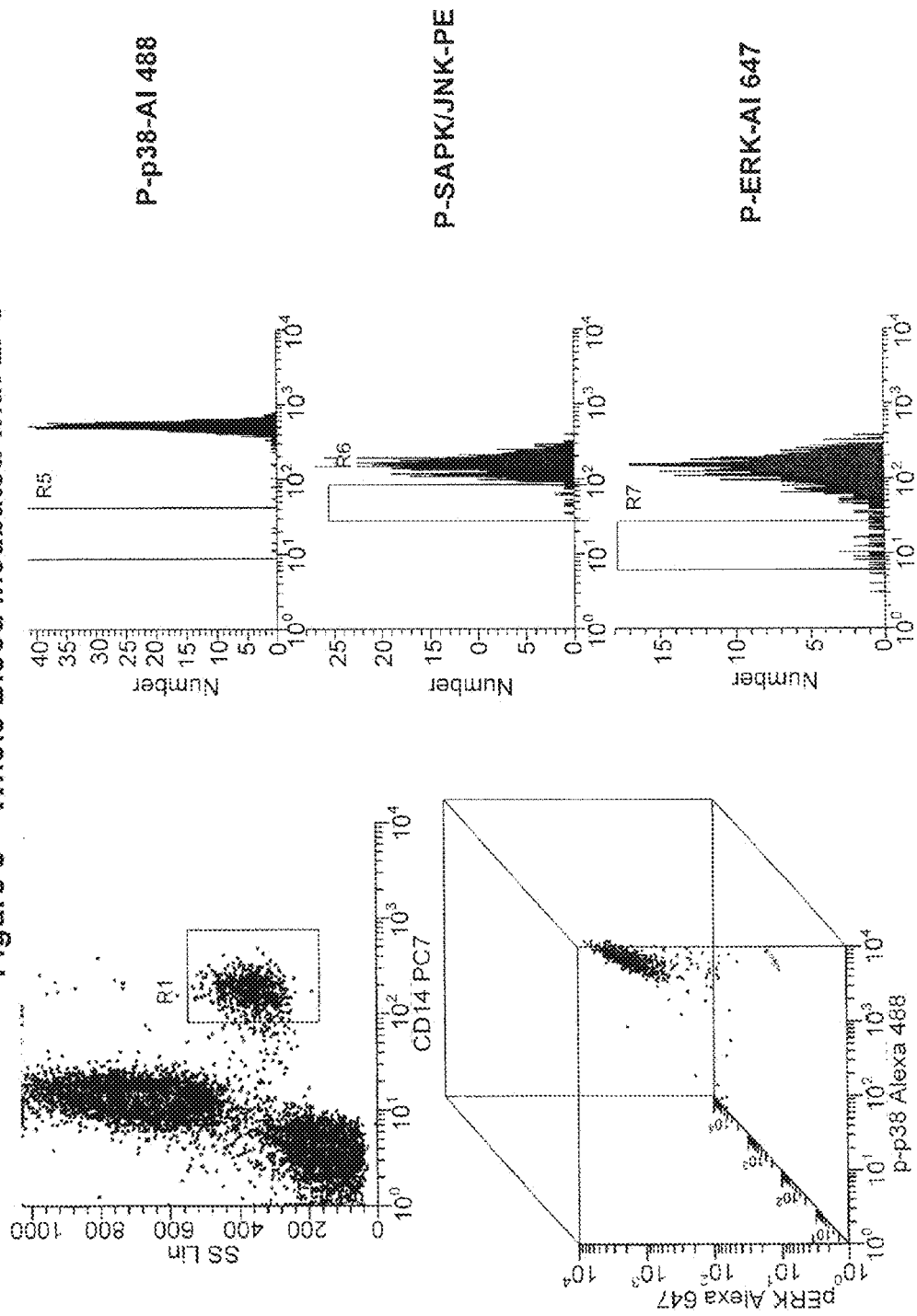
FIG. 3 shows normal whole blood stimulated with LPS for 10 minutes at 37° C., showing that all CD14+ monocytes have activated p-38, JNK, and ERK.
Figure 4:
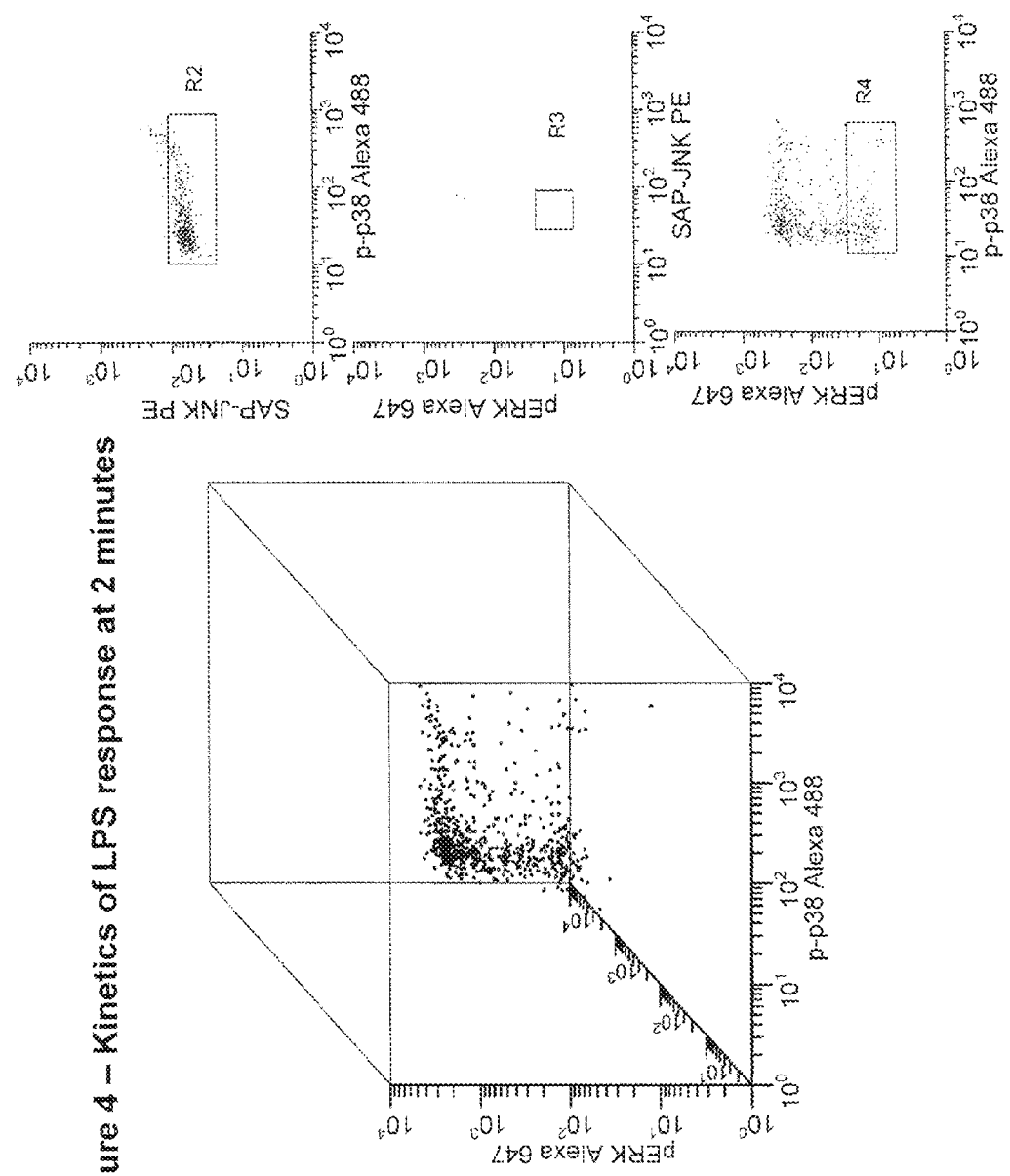
FIG. 4 shows the kinetics of LPS response in whole blood monocytes. ERK demonstrates the earliest activation shown here at 2 minutes following LPS stimulation at 37° C. before JNK or p38 activation.
Figure 5:
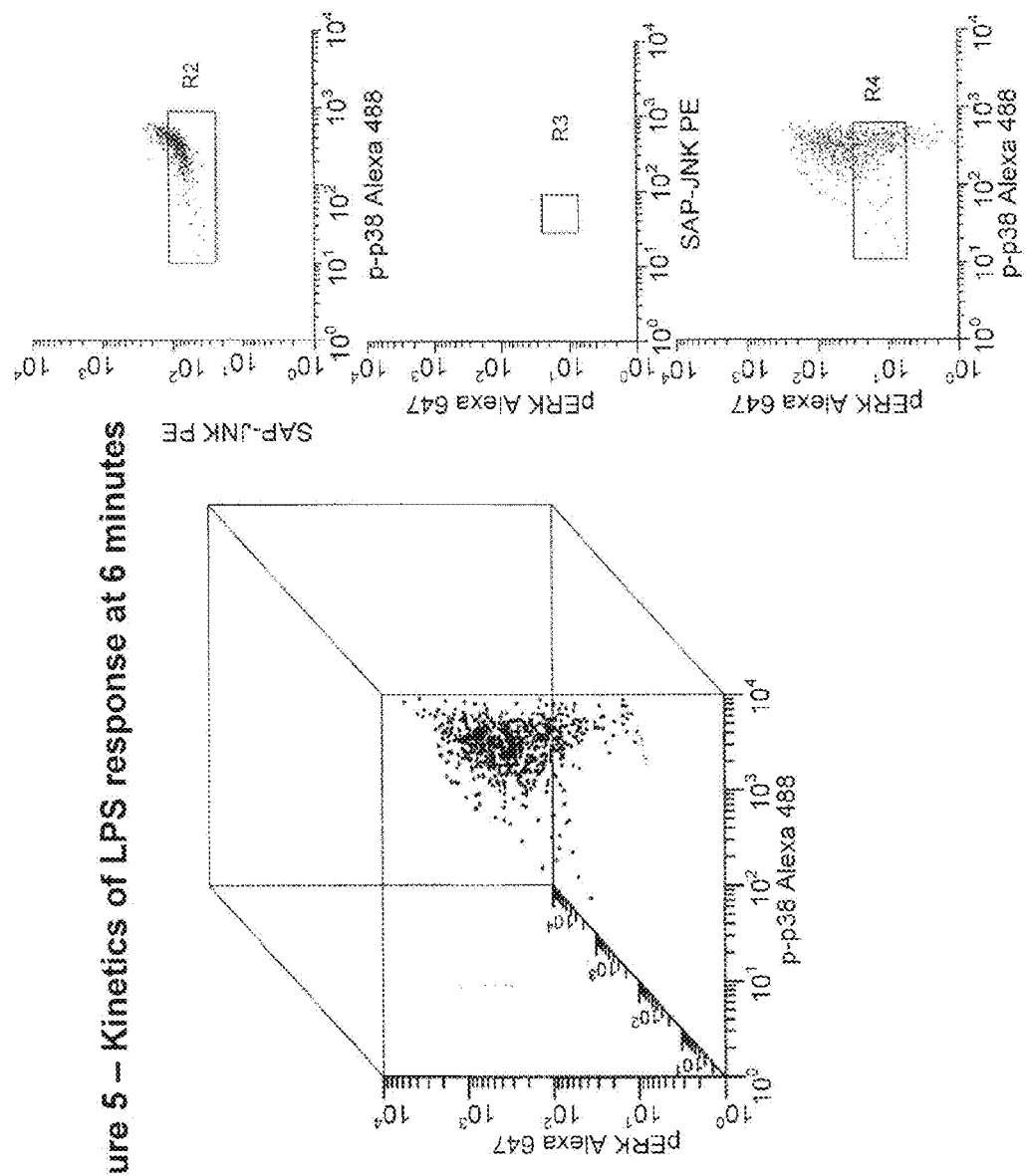
FIG. 5 shows the kinetics of LPS response in whole blood monocytes. Six minutes after LPS activation at 37° C. initial ERK activation declines. At later time points (about 10 minutes) p38, JNK and ERK increase.
Figure 6:
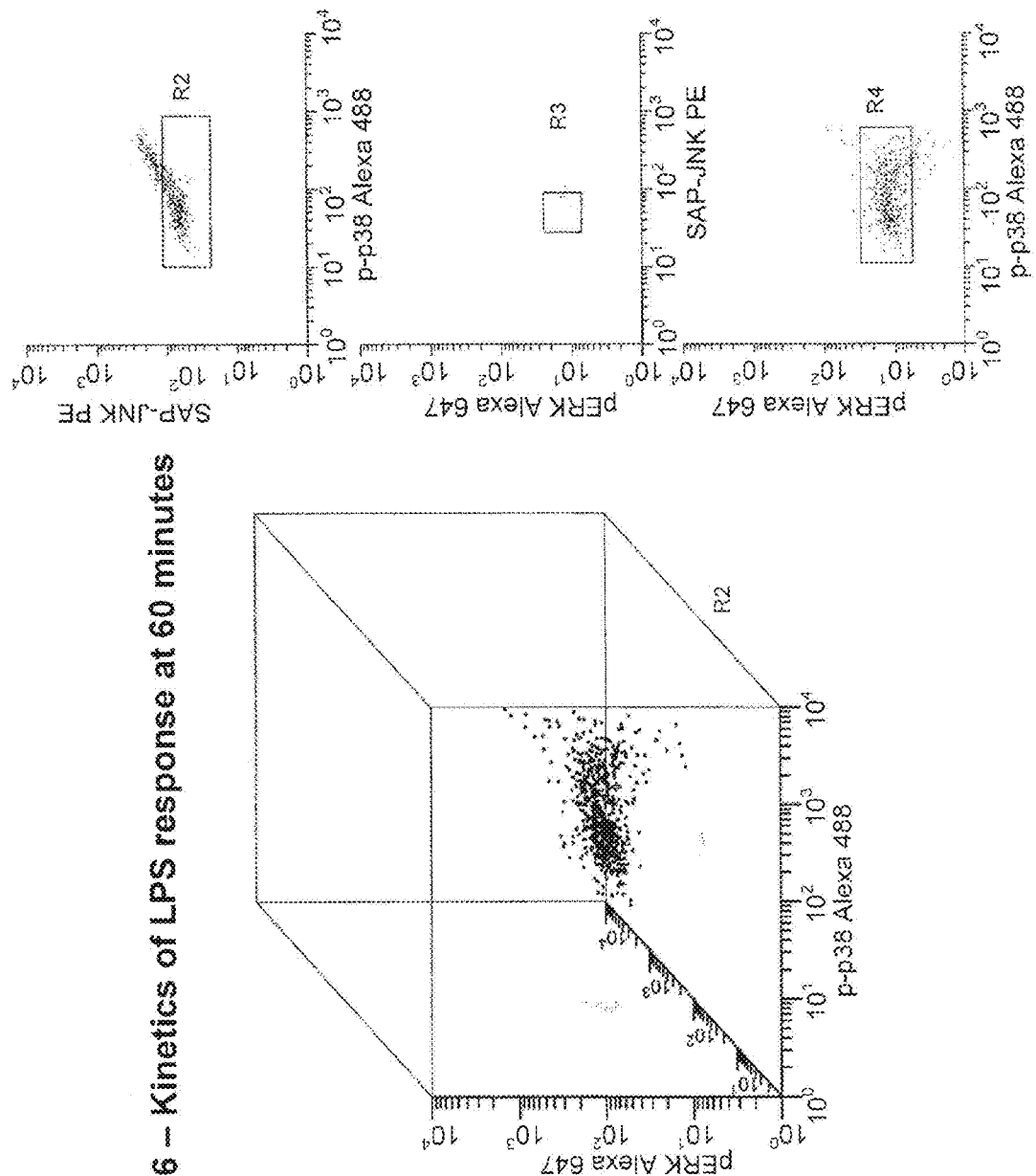
FIG. 6 shows the kinetics of LPS response. After 60 minutes of LPS activation, activity of all 3 MAPK pathways are decreased, but do not return to baseline. If additional LPS is added, no additional increase in any MAPK activity is seen. Re-stimulation with LPS (even up to 2 hours after in vitro stimulation with LPS) fails to increase signaling of these pathways.

Using the above-described techniques, unstimulated whole blood was found to express basal levels of several members of the MAPK pathway, including p38, SAPK/JNK, and ERK (FIG. 2). When similar samples were incubated with LPS, activation of the MAPK pathway was dramatic when compared to unstimulated controls (FIG. 3). Using the methods of the invention, the kinetics of LPS stimulation could be followed over time (FIGS. 4-6). ERK demonstrates the earliest activation shown here at 2 minutes following LPS stimulation at 37° C. before JNK or p38 activation (FIG. 4). Six minutes after LPS activation at 37° C. initial ERK activation declines (FIG. 5). At later time points(~10 minutes) p38,JNK and ERK increase. After 60 minutes of LPS activation, activity of all 3 MAPK pathways are decreased, but do not return to baseline (FIG. 6). If additional LPS is added, different MAP Kinase pathways show specific and characteristic patterns of response.

Figure 7:
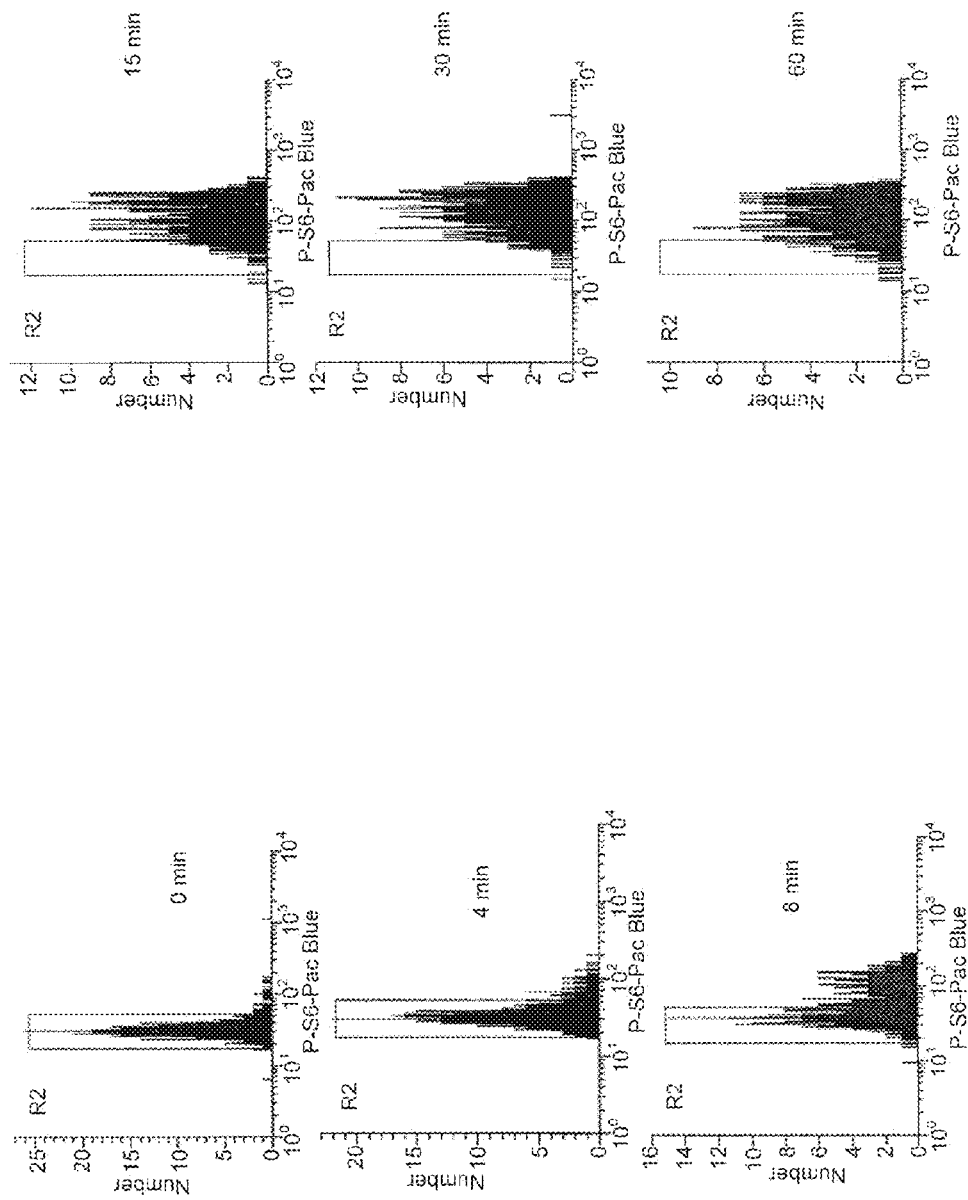
FIG. 7 shows the kinetics of ribosomal S6 protein activation in LPS stimulated monocytes. The peak activation of S6 is seen later than other MAPK pathway proteins.
Figure 8:
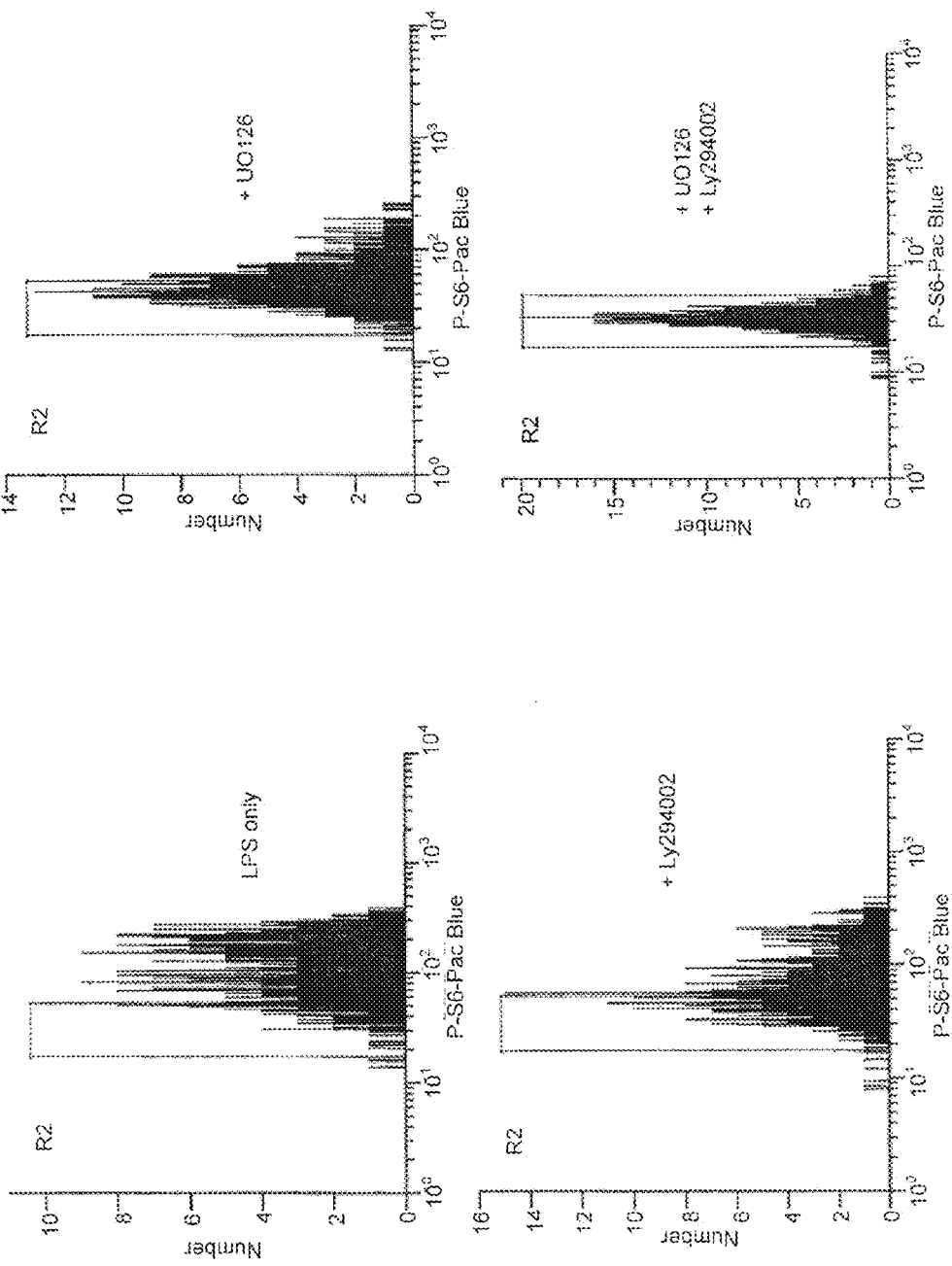
FIG. 8 shows inhibition of S6 activation by LPS with either the ERK inhibitor (U0126) or PI3K inhibitor (Ly294002) or both. Only inhibition of both pathways leads to complete inhibition of ribosomal S6 protein. Inhibition of ribosomal S6 is only accomplished by inhibition of both the ERK pathway (here using U0126) and the PI3K>Akt pathway (here using Ly294002). Complete inhibition of ribosomal S6 in the presence of both inhibitors provides additional evidence that PI3K is inhibited.

LPS stimulation also demonstrated patterns of inhibition of phosphorylation of the ribosomal S6 protein (FIG. 7). Phosphorylation of ribosomal S6 protein occurs at amino acids Ser235, Ser240, Ser244, and Ser247. The inhibition of phosphorylation was seen following the addition of both an ERK pathway inhibitor (e.g. U0126) and a PI3K inhibitor (e.g. LY294002), showing that both the ERK and Akt pathways must be inhibited to prevent LPS induced activation of ribosomal S6 protein (FIG. 8). These experiments demonstrate that LPS activation of whole blood can provide a rapid and practical technique to monitor all 3 MAPK pathways, plus PI3K (Akt) and NF kappa B activation. In particular, this approach provides a means to measure both in vitro and in vivo inhibition of these pathways by drugs (e.g. molecular targeted inhibitors of signaling pathways), and provides a means to monitor functional activity in monocytes (as a surrogate target) in patients receiving in vivo treatment with specific signal transduction pathway inhibitors.

Example 2

Flow Cytometry Based Sepsis Assay

In this study, a simultaneous measurement of four different signaling phospho-epitopes, which include P-ERK, P-p38 MAP Kinase, P-SAPK (Stress-Activated Protein Kinase), and P-S6 ribosomal protein (a measurement of new polypeptide synthesis), was conducted. This assay employed a measurement of the time course of LPS activation, in both "naive" whole blood, and whole blood samples previously exposed to LPS activation ("re-activated"). This assay also employed the fixation and permeabilization approach described above to measure both cell surface (CD14 to identify monocytes) and cytoplasmic or nuclear localized phospho-epitopes (P-ERK, P-p38, P-SAPK, and P-S6). This assay also employed an internal negative control to analyzing the data, relying on populations, rather than isotype controls, and measuring changes in MFI (mean fluorescence intensity) rather than percent positive.

The results from this study for each individual marker is presented below, followed by the improved utility of using the markers and analytical method employed in the study.

Figure 9:
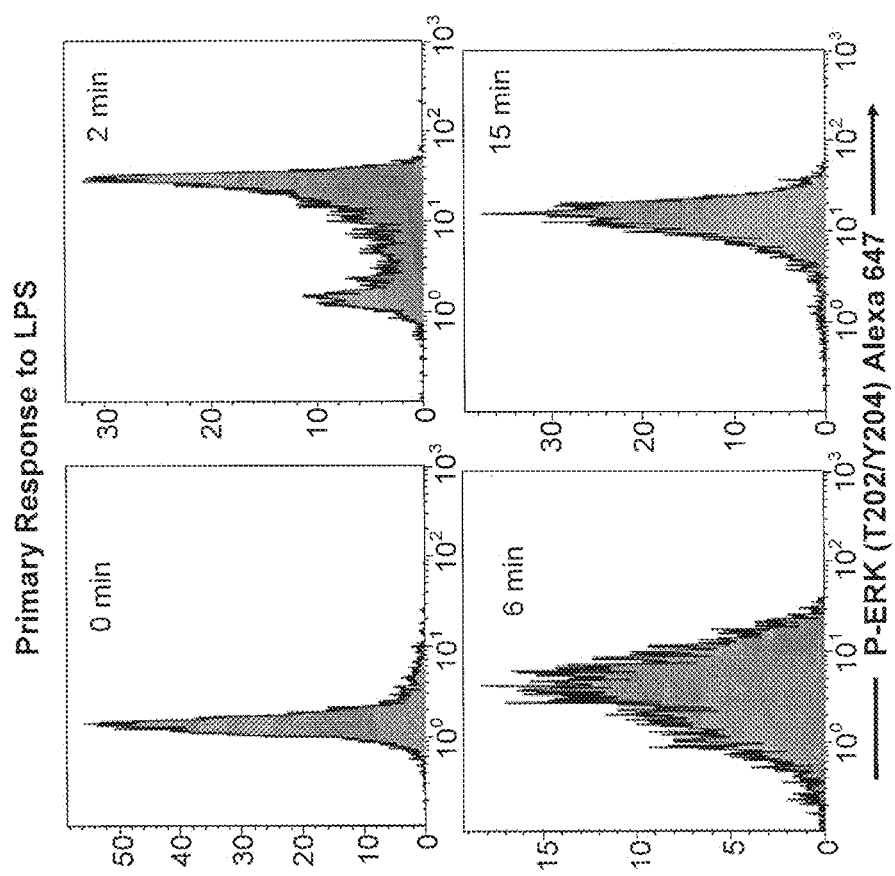
FIG. 9 shows that in normal samples (not previously exposed to LPS), LPS induces a rapid activation of ERK MAP Kinase, which is characterized by an early peak (1-4 minutes after LPS addition), a fall in P-ERK, and a second peak at 10-15 minutes after LPS stimulation. This second P-ERK peak occurs at the same time the levels of P-p38 and P-SAPK reach maximal levels.
Figure 10:
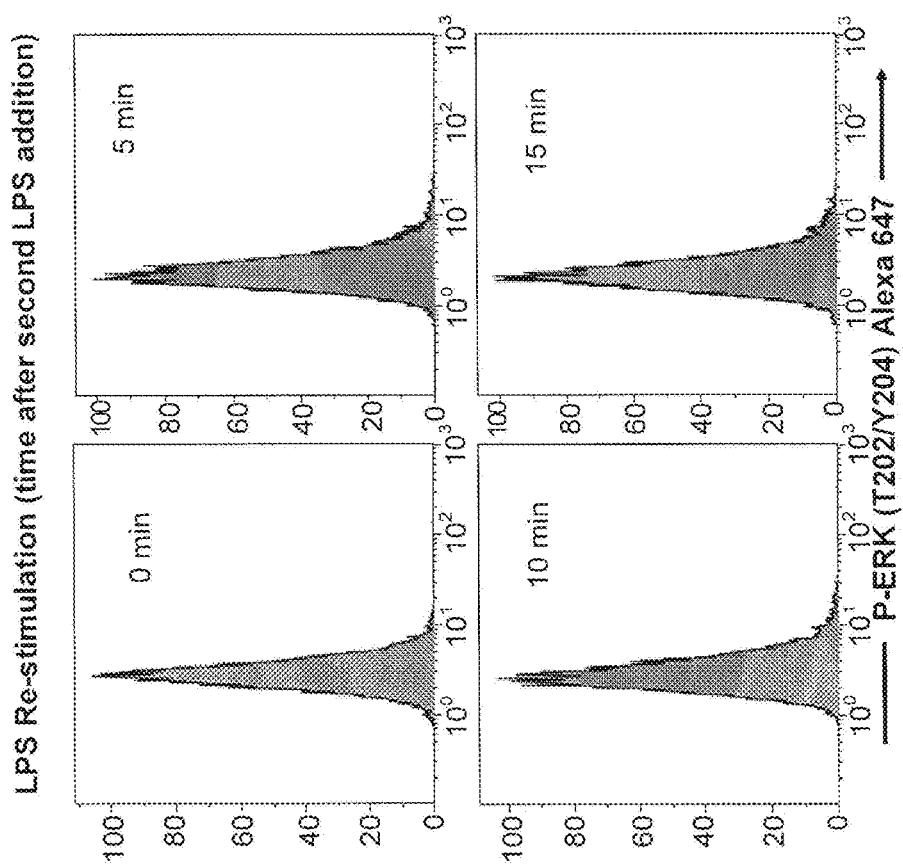
FIG. 10 shows that upon re-exposure to LPS, the mean fluorescent intensity (MFI) of P-ERK does not change significantly above the 0 time control for periods of up to 90 minutes after LPS re-stimulation.

P-ERK: As shown in FIG. 9, in normal samples (not previously exposed to LPS), LPS induces a rapid activation of ERK MAP Kinase, which is characterized by an early peak, a fall in P-ERK, and a second peak at 10-15 minutes after LPS stimulation. This second P-ERK peak occurs at the same time the levels of P-p38 and P-SAPK reach maximal levels. It is believed that the first P-ERK peak is driven through PI3 Kinase, while the second is likely through the classical MAPKKK>MAPKK>MAPK pathway from TLR4. When re-exposed to LPS (FIG. 10), the MFI of P-ERK does not change significantly above the 0 time control for periods of up to 90 minutes after LPS re-stimulation.

Figure 11:
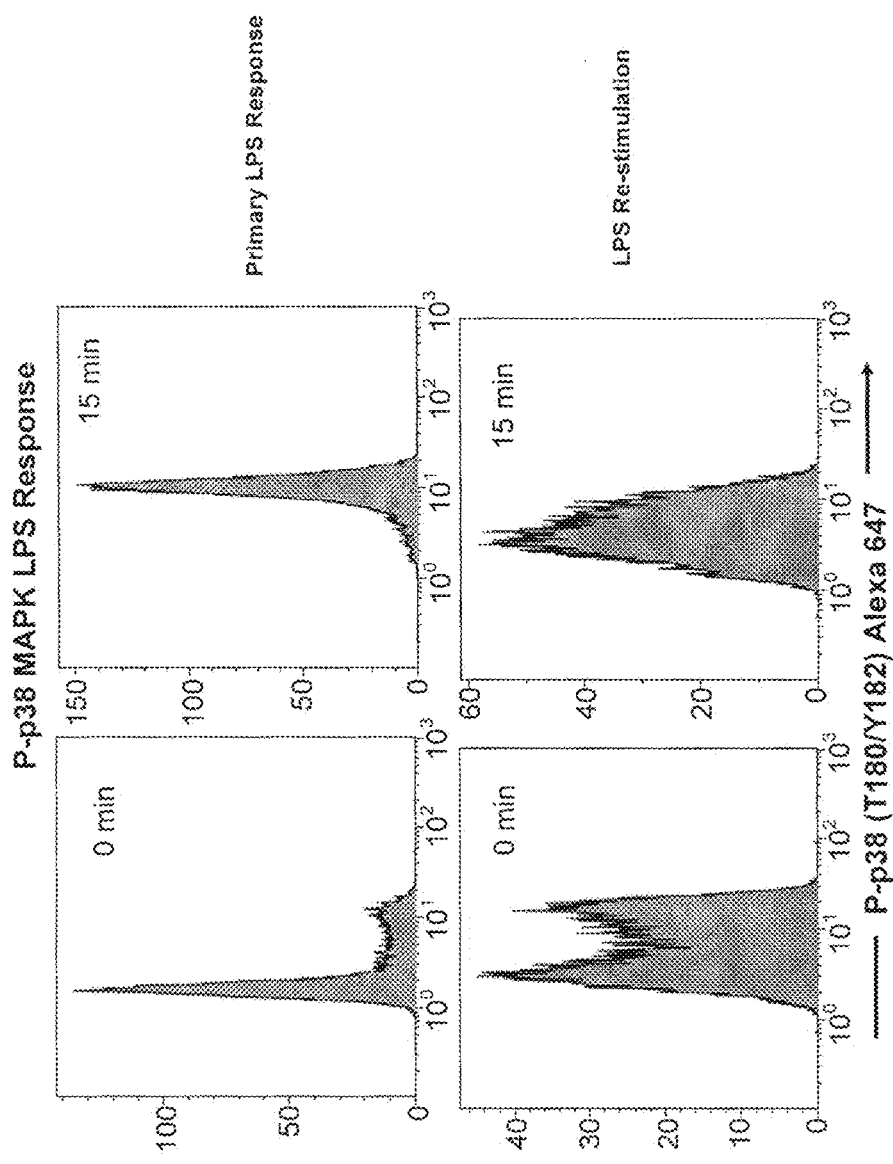
FIG. 11, top left, shows that approximately 10-15% of the monocytes (CD14+) expressing P-p38 in unstimulated whole blood samples from normal donors was detected. After primary LPS stimulation, the entire monocyte population (about 100%) shows a significant increase in MFI, with the response reaching a maximal MFI value at 15 minutes after LPS stimulation. The levels of P-p38 do not return to basal levels, even after periods of 120 min, showing the bimodal distribution seen in FIG. 11, lower left. After re-exposure to LPS the percentage of P-p38 positive monocytes increases from 40% (0 time, lower left) to 46% (15 min after LPS re-exposure, lower right). The aggregate MFI was 5.0 at the 0 time (lower left) and 5.5 15 minutes after re-exposure to LPS (lower right)

P-p38: Approximately 10-15% of the monocytes (CD14+) express P-p38 in unstimulated whole blood samples from normal donors (FIG. 11, top left). After primary LPS stimulation, the entire monocyte population (about 100%) shows a significant increase in MFI, with the response reaching a maximal MFI value at 15 minutes after LPS stimulation. The levels of P-p38 do not return to basal levels, even after periods of 120 min, showing the bimodal distribution seen in FIG. 11, lower left. Roughly 50% of the monocytes retain the same MFI as seen in the 15 min primary response, while the rest show MFI values of the major population in unstimulated samples, resulting in an aggregate MFI value between that of the positive and negative population. Following re-stimulation with LPS, the MFI value increases, peaking at 15-20 minutes after restimulation, then returning to a bi-modal population as seen 90-120 minutes after the initial LPS response.

Figure 12:
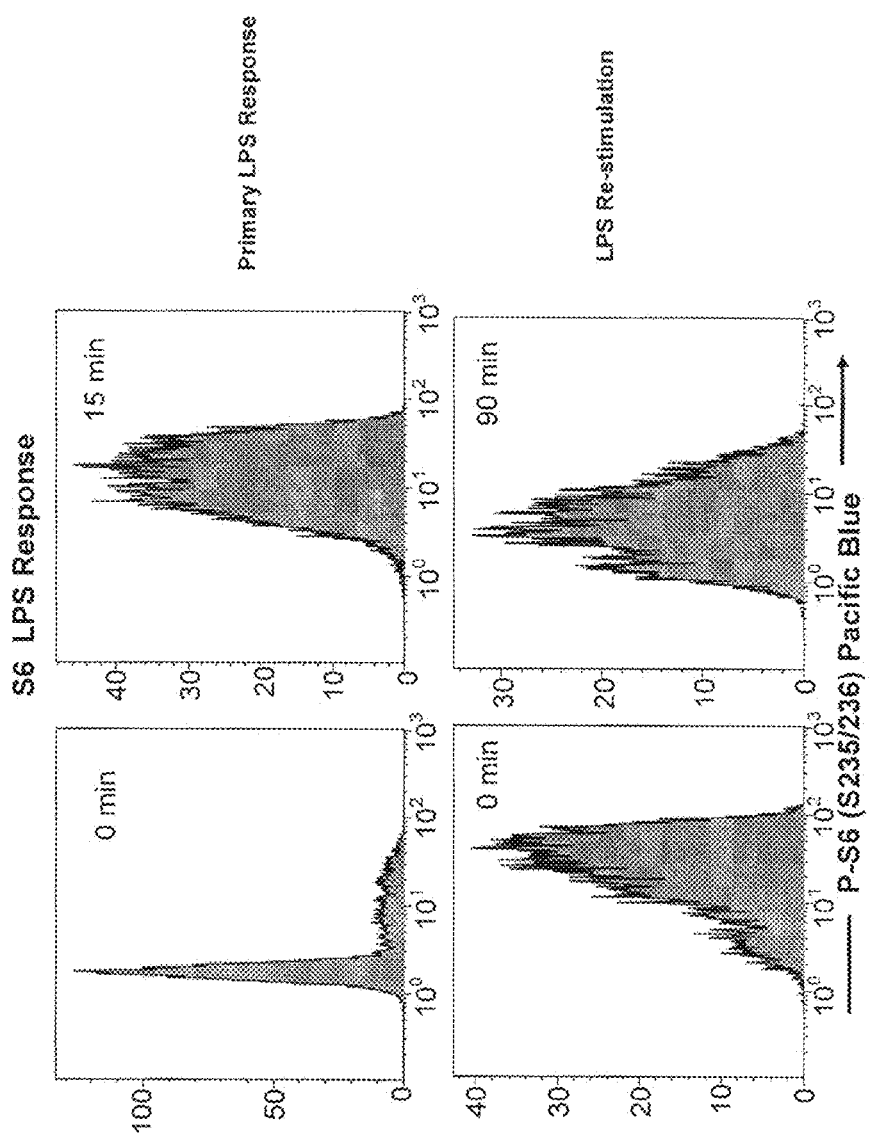
In FIG. 12, top left, in normal individuals, the level of P-S6 in unstimulated monocytes is low, with about 10% of the monocytes showing heterogeneous, positive levels of P-S6 expression. Levels of P-S6 peak after 15-60 minutes after LPS stimulation, consistent with its downstream activation secondary to P-ERK activation. Unlike P-ERK and P-p38, the levels of P-S6 persist for >120 minutes following LPS stimulation (FIG. 12, lower left). Following LPS re-stimulation, there is little change in the MFI of the P-S6 population, with a gradual decrease in MFI, as shown in FIG. 12, lower right.

P-S6: In normal individuals, the levels of P-S6 in unstimulated monocytes are low, with about 10% of the monocytes showing heterogeneous, positive levels of P-S6 expression (FIG. 12, top left). Levels of P-S6 peak after 15-30 minutes of LPS stimulation, consistent with its downstream activation secondary to P-ERK activation. Unlike P-ERK and P-p38, the levels of P-S6 persist for >120 minutes following LPS stimulation (FIG. 12, lower left). Following LPS re-stimulation, there is little change in the MFI of the P-S6 population, with a gradual decrease in MFI, as shown in FIG. 12, lower right.

P-SAPK: Levels of P-SAPK increase after initial LPS stimulation, peaking after 15 min. Similar to P-p38 levels, P-SAPK levels do not return to basal levels up to 120 minutes post stimulation, show 30-40% P-SAPK positive monocytes, with an aggregate MFI that reflects then combined values of the percentage and fluorescence intensity of the negative and positive populations.

While various embodiments of the invention have been described above, it should be understood that they have been presented by way of example only, and not limitation. It will be apparent to persons skilled in the relevant art that various changes in form and detail can be made therein without departing from the spirit and scope of the invention. Thus, the breadth and scope of the invention should not be limited by any of the above-described exemplary embodiments, but should be defined only in accordance with the following claims and their equivalents.

The invention claimed is:

1. A method of identifying and assessing the efficacy of an inhibitor of ribosomal S6 pathway activation, said method comprising the steps of:
   a) contacting a population of cells comprising a protein activated by the ribosomal S6 pathway with a first inhibitor, wherein said first inhibitor is a putative inhibitor of extracellular signal-related kinase (ERK) or phosphoinositide 3-kinase (PI3K);
   b) contacting said population of cells with a second inhibitor known to inhibit lipopolysaccharide activation of the ribosomal S6 pathway wherein said second inhibitor is an ERK inhibitor when said first inhibitor is a PI3K inhibitor and said second inhibitor is a PI3K inhibitor when said first inhibitor is an ERK inhibitor, wherein complete inhibition of LPS induced activation of ribosomal S6 pathway requires both of the ERK inhibitor and the PI3K inhibitor;
   c) contacting said population of cells with a lipopolysaccharide to activate said protein;

d) contacting said activated population of cells with a preservative;

e) unmasking intracellular epitopes of said preserved population of cells;

f) contacting said preserved and unmasked population of cells with a fluorescently labeled capture molecule being specific for the activated form of said protein;

g) detecting the fluorescence of the first putative inhibitor exposed cells indicative of binding of said labeled capture molecule to the activated form of said protein; and h) comparing the detected fluorescence of the first putative inhibitor exposed cells to detected fluorescence of a control cell sample comprising the protein that was not exposed to the first putative inhibitor but subjected to steps b) to f), wherein said first putative inhibitor is assessed to be an effective inhibitor of ribosomal S6 pathway activation if the detected fluorescence of the first putative inhibitor exposed cells is decreased relative to the detected fluorescence of the control sample not exposed to the first putative inhibitor.

2. The method according to claim 1, wherein said first inhibitor is an ERK inhibitor and said second inhibitor is a PI3K inhibitor.

3. The method according to claim 2, wherein said PI3K inhibitor is LY294002.

4. The method according to claim 1, wherein said first inhibitor is a PI3K inhibitor and said second inhibitor is an ERK inhibitor.

5. The method according to claim 4, wherein said ERK inhibitor is UO126.

6. The method according to claim 1, wherein said protein is a ribosomal S6 protein.

7. The method according to claim 6, wherein the activated form of said ribosomal S6 protein comprises phosphorylation at amino acids Ser235, Ser240, Ser244, or Ser247.

8. The method according to claim 7, wherein said second inhibitor is a known PI3K pathway inhibitor and wherein said first inhibitor is a putative ERK pathway inhibitor, and the capture molecule is an antibody specific for phosphorylated ribosomal 6 protein.

9. The method according to claim 7, wherein said second inhibitor is a known ERK pathway inhibitor and wherein said first inhibitor is a putative PI3K pathway inhibitor, and the capture molecule is an antibody specific for phosphorylated ribosomal 6 protein.

10. The method according to claim 1, wherein said second inhibitor is a known PI3K pathway inhibitor and said first inhibitor is a putative ERK pathway inhibitor, and wherein an amount of activation of said protein as measured by detected fluorescence is negatively correlated with efficacy of said first inhibitor.

11. The method according to claim 1, wherein said second inhibitor is a known ERK pathway inhibitor and said first inhibitor is a putative PI3K pathway inhibitor, and wherein an amount of activation of said protein as measured by the detected fluorescence is negatively correlated with the efficacy of said first inhibitor.

12. The method according to claim 1, wherein said first inhibitor is an inhibitor which has been or shall be administered to a patient.

13. The method according to claim 1, wherein said population of cells comprises monocytes.

14. The method according to claim 1, further comprising the step of permeabilizing said population of cells following the contacting said activated population of cells with a preservative.

15. The method according to claim 1, wherein efficacy of said first inhibitor is assessed by administration in vivo or in vitro.

16. The method according to claim 1, wherein flow cytometry is used to detect binding of said labeled capture molecule to said protein.

17. The method according to claim 1, wherein efficacy of said first inhibitor is assessed at multiple time points.

18. The method according to claim 1, wherein said labeled capture molecule is a labeled antibody.

19. The method according to claim 1, wherein unmasking comprises contacting the population of cells with an alcohol and a detergent.

20. The method according to claim 19, wherein said alcohol is at a concentration of about 25 percent to about 90 percent.

21. The method according to claim 19, wherein said alcohol comprises ethanol or methanol.

22. The method according to claim 19, wherein said detergent is at a concentration of about 0.1 percent to about 10 percent.

23. The method according to claim 22, wherein said detergent comprises ethyoxylated octyphenol, octylphenoxypoly (ethyleneoxy)ethanol, or a linear alcohol alkoxylate.

24. The method according to claim 1, wherein the preservative comprises aldehyde, paraformaldehyde, or formaldehyde.

* * * * *